United States Patent
Fainzilber et al.

(10) Patent No.: US 6,624,288 B1
(45) Date of Patent: Sep. 23, 2003

(54) GAMMA-CONOPEPTIDES

(75) Inventors: Michael Fainzilber, Haifa (IL); Karel S. Kits, Amsterdam (NL); Alma L. Burlingame, Sausalito, CA (US); Baldomero M. Olivera, Salt Lake City, UT (US); Craig Walker, Salt Lake City, UT (US); Maren Watkins, Salt Lake City, UT (US); Reshma Shetty, Salt Lake City, UT (US); Lourdes J. Cruz, Manila (PH); Julita Imperial, Salt Lake City, UT (US); Clark Colledge, Draper, UT (US)

(73) Assignees: Cognetix, Inc., Salt Lake City, UT (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/210,952

(22) Filed: Dec. 15, 1998

Related U.S. Application Data
(60) Provisional application No. 60/069,706, filed on Dec. 16, 1997.

(51) Int. Cl.$^7$ ................................................ C07K 5/00
(52) U.S. Cl. ...................................... 530/324; 530/357
(58) Field of Search ................................ 530/300, 324, 530/357

(56) References Cited

U.S. PATENT DOCUMENTS

| 5,432,155 A | 7/1995 | Olivera et al. |
| 5,889,147 A | 3/1999 | Cruz et al. |

OTHER PUBLICATIONS

Shen et al., Conopeptides: From deadly venoms to novel therapeutics, Drug Discovery Today, 5(3):98–106, Mar. 2000.*
Eldridge et al., J. of Virology, 66(11):6563–6571, Nov. 1992.*
Fainzilber, M. et al. (1995). "A new cysteine framework in sodium channel blocking conotoxins." *Biochem.* 34:8649–56.
Fainzilber, M. et al. (1995). "A new conotoxin affecting sodium current inactivation interacts with the δ–contotoxin receptor site." *J. Biol. Chem.* 270:1123–29.
Nakamura, T. et al. (1996). "Mas spectormetric–based revision of the structure of a cysteine–rich peptide toxin with γ–carboxyglutamic acid, TxVIIA, from the sea snail, *Conus textile.*" *Protein Science* 5:524–30.
Fainzilber, M. et al. (1991), "Mollusc–specific toxins from the venom of *Conus textile neovicarius.*" *Eur. J. Biochem.* 202:589–95.

Partridge, L.D. and Swandulla, D. (1988). "Calcium–activated non–specific cation channels." *Trends in Neurosci.* 11:69–72.

Kits, K.S. and Mansvelder, H.D. (1996). "Voltage gated calcium channels in molluscs: classification, $Ca^{2+}$ deptendent inactivation, modulation and functional roles." *Invertebrate Neurosci.* 2:9–34.

Reuter, H. (1984). "Ion channels in cardiac cell membranes." *Ann. Rev. Physiol.* 46:473–84.

Hoehn, K. et al. (1993). A novel tetrodotoxin–insensitive, slow sodium current in striatal and hippocampal neurons. *Neuron* 10:543–52.

* cited by examiner

*Primary Examiner*—Patrick J. Nolan
(74) *Attorney, Agent, or Firm*—Rothwell, Figg, Ernst & Manbeck

(57) ABSTRACT

This invention relates to relatively short peptides about 25–40 residues in length, which are naturally available in minute amounts in the venom of the cone snails or analogs to the naturally available peptides, and which include three cyclizing disulfide linkages and one or more γ-carboxyglutamate residues. More specifically, the present invention is directed to γ-conopeptides having the general formula I: $Xaa_1$-Cys-$Xaa_2$-Cys-$Xaa_3$-$Xaa_4$-Cys-Cys-$Xaa_5$-Cys-$Xaa_6$-Cys-$Xaa_7$ (SEQ ID NO:1), as described herein; or having the general formula II: $Xaa_1$-Cys-$Xaa_2$-Cys-$Xaa_3$-$Xaa_4$-Cys-Cys-$Xaa_5$-$Xaa_6$-Cys-$Xaa_7$-Cys-$Xaa_8$ (SEQ ID NO:2), as defined herein; or having the general formula III: $Xaa_1$-Cys-$Xaa_2$-Cys-$Xaa_3$-$Xaa_4$-$Xaa_5$-Cys-Cys-Ser-Asn-Ser-Cys-Asp-$Xaa_2$-Cys-$Xaa_7$ (SEQ ID NO:3), as described herein; or having the general formula IV: $Xaa_1$-Cys-$Xaa_2$-Cys-$Xaa_3$-$Xaa_4$-$Xaa_5$-Cys-Cys-Ser-Asn-Ser-Cys-Asp-$Xaa_6$-Cys-$Xaa_7$ (SEQ ID NO:4), as described herein; or having the general formula V: $Xaa_1$-$Xaa_2$-Cys-$Xaa_3$-$Xaa_4$-Phe-$Xaa_5$-Cys-Thr-$Xaa_6$-Ser-$Xaa_7$-Cys-Cys-Ser-Asn-Ser-Cys-Asp-Gln-Thr-Tyr-Cys-$Xaa_8$-Leu-$Xaa_9$ (SEQ ID NO:5), as described herein. The invention further relates to specific γ-conopeptides, specific pro-γ-conopeptides and nucleic acids encoding the pro-γ-conopeptides. The invention also includes pharmaceutically acceptable salts of the conopeptides. These conopeptides are useful as agonists of neuronal pacemaker calcium channels.

9 Claims, No Drawings

SEQUENCE LISTING

<160> NUMBER OF SEQ ID NOS: 47

<210> SEQ ID NO 1
<211> LENGTH: 42
<212> TYPE: PRT
<213> ORGANISM: Artificial Sequence
<220> FEATURE:
<223> OTHER INFORMATION: Description of Artificial Sequence:generic
      formula of gamma-conopeptides
<220> FEATURE:
<221> NAME/KEY: PEPTIDE
<222> LOCATION: (1)..(13)
<223> OTHER INFORMATION: Xaa at residues 1, 2, 3, 4, 5, and 6 may be
      des-Xaa or any amino acid; Xaa at residues 8, 9, 10, 11 and 12 may
      be any amino acid; Xaa at residue 13 may be des-Xaa or any amino
      acid.
<220> FEATURE:
<221> NAME/KEY: PEPTIDE
<222> LOCATION: (15)..(19)
<223> OTHER INFORMATION: Xaa at residues 15, 16, 17 and 18 may be any
      amino acid; Xaa at residue 19 is Glu, gamma-carboxyglutamate or
      Gln.
<220> FEATURE:
<221> NAME/KEY: PEPTIDE
<222> LOCATION: (22)..(28)
<223> OTHER INFORMATION: Xaa at residues 22, 23 and 24 may be any amino
      acid; Xaa at residue 25 may be des-Xaa or any amino acid; Xaa at
      residues 27, 28 and 29 may be any amino acid.
<220> FEATURE:
<221> NAME/KEY: PEPTIDE
<222> LOCATION: (30)..(42)
<223> OTHER INFORMATION: Xaa at residues 30, 31 and 32 may be des-Xaa or
      any amino acid; Xaa at residues 34 and 35 may be any amino acid;
      Xaa at residues 36, 37, 38, 39, 40, 41 and 42 may be des-Xaa or
      any amino acid.

<400> SEQUENCE: 1

Xaa Xaa Xaa Xaa Xaa Xaa Cys Xaa Xaa Xaa Xaa Xaa Xaa Cys Xaa Xaa
 1               5                  10                  15

Xaa Xaa Xaa Cys Cys Xaa Xaa Xaa Xaa Cys Xaa Xaa Xaa Xaa Xaa Xaa
             20                  25                  30

Cys Xaa Xaa Xaa Xaa Xaa Xaa Xaa Xaa Xaa
         35                  40

<210> SEQ ID NO 2
<211> LENGTH: 42
<212> TYPE: PRT
<213> ORGANISM: Artificial Sequence
<220> FEATURE:
<223> OTHER INFORMATION: Description of Artificial Sequence:generic
      sequence of gamma-conopeptides.
<220> FEATURE:
<221> NAME/KEY: PEPTIDE
<222> LOCATION: (1)..(13)
<223> OTHER INFORMATION: Xaa at residues 1, 2, 3, 4, 5 and 6 may be
      des-Xaa or any amino acid; Xaa at residues 8, 9, 10, 11 and 12 may
      be any amino acid; Xaa at residue 13 may be des-Xaa or any amino
      acid.
<220> FEATURE:
<221> NAME/KEY: PEPTIDE
<222> LOCATION: (15)..(22)
<223> OTHER INFORMATION: Xaa at residues 15, 16, 17 and 18 may be any
      amino acid; Xaa at residue 19 is Glu, gamma-carboxyglutamate or
      Gln; Xaa at residue 22 is Ser or Thr.
<220> FEATURE:
<221> NAME/KEY: PEPTIDE
<222> LOCATION: (23)..(29)
<223> OTHER INFORMATION: Xaa at residues 23 and 24 may be any amino
      acid; Xaa at residue 25 may be des-Xaa or any amino acid; Xaa at
      residues 27, 28 and 29 may be any amino acid.
<220> FEATURE:
<221> NAME/KEY: PEPTIDE

```
<222> LOCATION: (30)..(42)
<223> OTHER INFORMATION: Xaa at residues 30, 31 and 32 may be des-Xaa or
      any amino acid; Xaa at residues 34 and 35 may be any amino acid;
      Xaa at residues 36, 37, 38, 39, 40, 41 and 42 may be des-Xaa or
      any amino acid.

<400> SEQUENCE: 2

Xaa Xaa Xaa Xaa Xaa Xaa Cys Xaa Xaa Xaa Xaa Xaa Cys Xaa Xaa
 1               5                  10                  15

Xaa Xaa Xaa Cys Cys Xaa Xaa Xaa Cys Xaa Xaa Xaa Xaa Xaa
            20                  25                  30

Cys Xaa Xaa Xaa Xaa Xaa Xaa Xaa Xaa
        35                  40

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence:generic
      formula of gamma-conopeptides
<220> FEATURE:
<221> NAME/KEY: PEPTIDE
<222> LOCATION: (1)..(13)
<223> OTHER INFORMATION: Xaa at residue 1 is any amino acid; Xaa at
      residues 2, 3, 4, 5 and 6 may be des-Xaa or any amino acid; Xaa at
      residues 8, 9, 10, 11, 12 and 13 may be any amino acid.
<220> FEATURE:
<221> NAME/KEY: PEPTIDE
<222> LOCATION: (27)..(39)
<223> OTHER INFORMATION: Xaa at residues 27, 28, 29, 31, 32, 33, 34, 35,
      36 and 37 may be any amino acid; Xaa at residues 38 and 39 may be
      des-Xaa or any amino acid.
<220> FEATURE:
<221> NAME/KEY: PEPTIDE
<222> LOCATION: (15)..(19)
<223> OTHER INFORMATION: Xaa at residues 15, 16, 17 and 18 may be any
      amino acid; Xaa at residue 19 is Glu, gamma-carboxyglutamate or
      Gln.

<400> SEQUENCE: 3

Xaa Xaa Xaa Xaa Xaa Xaa Cys Xaa Xaa Xaa Xaa Xaa Cys Xaa Xaa
 1               5                  10                  15

Xaa Xaa Xaa Cys Cys Ser Asn Ser Cys Asp Xaa Xaa Xaa Cys Xaa Xaa
            20                  25                  30

Xaa Xaa Xaa Xaa Xaa Xaa Xaa
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence:generic
      sequence of gamma-conopeptides.
<220> FEATURE:
<221> NAME/KEY: PEPTIDE
<222> LOCATION: (1)..(13)
<223> OTHER INFORMATION: Xaa at residue 1 is any amino acid; Xaa at
      residues 2, 3, 4, 5 and 6 may be des-Xaa or any amino acid; Xaa at
      residues 8, 9, 10, 11, 12 and 13 may be any amino acid.
<220> FEATURE:
<221> NAME/KEY: PEPTIDE
<222> LOCATION: (15)..(19)
<223> OTHER INFORMATION: Xaa at residue 15 is Ser or Thr; Xaa at
      residues 16, 17 and 18 may ba any amino acid; Xaa at residue 19 is
      Glu, gamma-carboxyglutamate or Gln.
<220> FEATURE:
<221> NAME/KEY: PEPTIDE
<222> LOCATION: (27)..(39)
<223> OTHER INFORMATION: Xaa at residues 27, 28, 29, 31, 32, 33, 34, 35,
```

36 and 37 may be any amino acid; Xaa at residues 38 and 39 may be des-Xaa or any amino acid.

<400> SEQUENCE: 4

Xaa Xaa Xaa Xaa Xaa Xaa Cys Xaa Xaa Xaa Xaa Xaa Xaa Cys Xaa Xaa
 1               5                  10                  15

Xaa Xaa Xaa Cys Cys Ser Asn Ser Cys Asp Xaa Xaa Xaa Cys Xaa Xaa
             20                  25                  30

Xaa Xaa Xaa Xaa Xaa Xaa Xaa
         35

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence:generic
      sequence of gamma-conopeptides.
<220> FEATURE:
<221> NAME/KEY: PEPTIDE
<222> LOCATION: (1)..(6)
<223> OTHER INFORMATION: Xaa at residues 1 and 2 may be des-Xaa or a any
      amino acid; Xaa at residue 3 is Asp, Glu or
      gamma-carboxyglutamate; Xaa at residues 5 and 6 may be any amino
      acid.
<220> FEATURE:
<221> NAME/KEY: PEPTIDE
<222> LOCATION: (7)..(16)
<223> OTHER INFORMATION: Xaa at residue 7 is Trp or 6-bromo-Trp; Xaa at
      residues 9, 10, 13 and 14 may be any amino acid; Xaa at residue 16
      is Glu, gamma-carboxyglutamate or Gln.
<220> FEATURE:
<221> NAME/KEY: PEPTIDE
<222> LOCATION: (28)..(34)
<223> OTHER INFORMATION: Xaa at residues 28, 30, 31, 32, 33 and 34 may
      be any amino acid.

<400> SEQUENCE: 5

Xaa Xaa Xaa Cys Xaa Xaa Xaa Phe Xaa Xaa Cys Thr Xaa Xaa Ser Xaa
 1               5                  10                  15

Cys Cys Ser Asn Ser Cys Asp Trp Thr Tyr Cys Xaa Leu Xaa Xaa Xaa
             20                  25                  30

Xaa Xaa

<210> SEQ ID NO 6
<211> LENGTH: 32
<212> TYPE: PRT
<213> ORGANISM: Conus pennaceus
<220> FEATURE:
<221> NAME/KEY: PEPTIDE
<222> LOCATION: (1)..(31)
<223> OTHER INFORMATION: Xaa at residue 5 is Trp or 6-bromo-Trp; Xaa at
      residues 14 and 26 are Glu or gamma-carboxyglutamate; Xaa at
      residue 31 is Pro or hydroxy-Pro.

<400> SEQUENCE: 6

Asp Cys Thr Ser Xaa Phe Gly Arg Cys Thr Val Asn Ser Xaa Cys Cys
 1               5                  10                  15

Ser Asn Ser Cys Asp Gln Thr Tyr Cys Xaa Leu Tyr Ala Phe Xaa Ser
             20                  25                  30

<210> SEQ ID NO 7
<211> LENGTH: 34
<212> TYPE: PRT
<213> ORGANISM: Conus textile
<220> FEATURE:
<221> NAME/KEY: PEPTIDE
<222> LOCATION: (1)..(34)

```
<223> OTHER INFORMATION: Xaa at residues 1, 7 and 34 are Trp or
      6-bromo-Trp; Xaa at residues 3 and 16 are Glu or
      gamma-carboxyglutamate; Xaa at residues 31 and 32 are Pro or
      hydroxy-Pro.

<400> SEQUENCE: 7

Xaa Leu Xaa Cys Ser Val Xaa Phe Ser His Cys Thr Lys Asp Ser Xaa
 1               5                  10                  15

Cys Cys Ser Asn Ser Cys Asp Gln Thr Tyr Cys Thr Leu Met Xaa Xaa
                20                  25                  30

Asp Xaa

<210> SEQ ID NO 8
<211> LENGTH: 39
<212> TYPE: PRT
<213> ORGANISM: Conus textile
<220> FEATURE:
<221> NAME/KEY: PEPTIDE
<222> LOCATION: (1)..(39)
<223> OTHER INFORMATION: Xaa at residues 1, 2, 4, 10 and 39 are Trp or
      6-bromo-Trp ; Xaa at residues 19 and 31 are Glu or
      gammacarboxyglutamate; Xaa at residues 34, 36 and 37 ar Pro or
      hydroxy-Pro.

<400> SEQUENCE: 8

Xaa Xaa Arg Xaa Gly Gly Cys Met Ala Xaa Phe Gly Leu Cys Ser Arg
 1               5                  10                  15

Asp Ser Xaa Cys Cys Ser Asn Ser Cys Asp Val Thr Arg Cys Xaa Leu
                20                  25                  30

Met Xaa Phe Xaa Xaa Asp Xaa
            35

<210> SEQ ID NO 9
<211> LENGTH: 27
<212> TYPE: PRT
<213> ORGANISM: Conus textile
<220> FEATURE:
<221> NAME/KEY: PEPTIDE
<222> LOCATION: (1)..(27)
<223> OTHER INFORMATION: Xaa at residues 9, 13 and 17 are Glu or
      gamma-carboxyglutamate.

<400> SEQUENCE: 9

Cys Lys Thr Tyr Ser Lys Tyr Cys Xaa Ala Asp Ser Xaa Cys Cys Thr
 1               5                  10                  15

Xaa Gln Cys Val Arg Ser Tyr Cys Thr Leu Phe
                20                  25

<210> SEQ ID NO 10
<211> LENGTH: 34
<212> TYPE: PRT
<213> ORGANISM: Conus textile
<220> FEATURE:
<221> NAME/KEY: PEPTIDE
<222> LOCATION: (1)..(34)
<223> OTHER INFORMATION: Xaa at residues 2, 3, 10 and 32 are Trp or
      6-bromo-Trp; Xaa at residues 18, 26 and 33 are Glu or
      gamma-carboxyglutamate; Xaa at residue 12 is Pro or hydroxy-Pro.

<400> SEQUENCE: 10

Asp Xaa Xaa Asp Asp Gly Cys Ser Val Xaa Gly Xaa Cys Thr Tyr Asn
 1               5                  10                  15

Ala Xaa Cys Cys Ser Gly Asp Cys His Xaa Thr Cys Ile Phe Gly Xaa
                20                  25                  30

Xaa Val
```

```
<210> SEQ ID NO 11
<211> LENGTH: 31
<212> TYPE: PRT
<213> ORGANISM: Conus textile
<220> FEATURE:
<221> NAME/KEY: PEPTIDE
<222> LOCATION: (1)..(31)
<223> OTHER INFORMATION: Xaa at residues 3 and 31 are Trp of
      6-bromo-Trp; Xaa at residues 5, 18, 22 and 25 are Glu or
      gamma-carboxyglutamate; Xaa at residue 16 is Pro or hydroxy-Pro.

<400> SEQUENCE: 11

Gly Met Xaa Gly Xaa Cys Lys Asp Gly Leu Thr Thr Cys Leu Ala Xaa
  1               5                  10                  15

Ser Xaa Cys Cys Ser Xaa Asp Cys Xaa Gly Ser Cys Thr Met Xaa
             20                  25                  30

<210> SEQ ID NO 12
<211> LENGTH: 32
<212> TYPE: PRT
<213> ORGANISM: Conus gloriamaris
<220> FEATURE:
<221> NAME/KEY: PEPTIDE
<222> LOCATION: (1)..(32)
<223> OTHER INFORMATION: Xaa at residue 5 is Trp or 6-bromo-Trp; Xaa at
      residue 1 is Glu or gamma-carboxyglutamate; Xaa at residues 8 and
      11 are Pro or hydroxy-Pro.

<400> SEQUENCE: 12

Xaa Cys Arg Ala Xaa Tyr Ala Xaa Cys Ser Xaa Gly Ala Gln Cys Cys
  1               5                  10                  15

Ser Leu Leu Met Cys Ser Lys Ala Thr Ser Arg Cys Ile Leu Ala Leu
             20                  25                  30

<210> SEQ ID NO 13
<211> LENGTH: 29
<212> TYPE: PRT
<213> ORGANISM: Conus marmoreus
<220> FEATURE:
<221> NAME/KEY: PEPTIDE
<222> LOCATION: (1)..(29)
<223> OTHER INFORMATION: Xaa at residues 8 and 15 are Trp or
      6-bromo-Trp; Xaa at residues 5, 16 and 23 are Glu or
      gamma-carboxyglutamate; Xaa at residue 10 is Pro or hydroxy-Pro.

<400> SEQUENCE: 13

Asn Gly Gln Cys Xaa Asp Val Xaa Met Xaa Cys Thr Ser Asn Xaa Xaa
  1               5                  10                  15

Cys Cys Ser Leu Asp Cys Xaa Met Tyr Cys Thr Gln Ile
             20                  25

<210> SEQ ID NO 14
<211> LENGTH: 27
<212> TYPE: PRT
<213> ORGANISM: Conus marmoreus
<220> FEATURE:
<221> NAME/KEY: PEPTIDE
<222> LOCATION: (1)..(27)
<223> OTHER INFORMATION: Xaa at residue 4 is Trp or 6-bromo-Trp; Xaa at
      residues 9, 12, 13 and 17 are Glu or gamma-carboxyglutamate.

<400> SEQUENCE: 14

Cys Gly Gly Xaa Ser Thr Tyr Cys Xaa Val Asp Xaa Xaa Cys Cys Ser
  1               5                  10                  15

Xaa Ser Cys Val Arg Ser Tyr Cys Thr Leu Phe
             20                  25
```

<210> SEQ ID NO 15
<211> LENGTH: 26
<212> TYPE: PRT
<213> ORGANISM: Conus marmoreus
<220> FEATURE:
<221> NAME/KEY: PEPTIDE
<222> LOCATION: (1)..(26)
<223> OTHER INFORMATION: Xaa at residues 8 and 15 are Trp or
      6-bromo-Trp; Xaa at residue 16 is Glu or gamma-carboxyglutamate.

<400> SEQUENCE: 15

Asn Gly Gly Cys Lys Ala Thr Xaa Met Ser Cys Ser Ser Gly Xaa Xaa
 1               5                  10                  15

Cys Cys Ser Met Ser Cys Asp Met Tyr Cys
            20                  25

<210> SEQ ID NO 16
<211> LENGTH: 323
<212> TYPE: DNA
<213> ORGANISM: Conus textile
<220> FEATURE:
<221> NAME/KEY: CDS
<222> LOCATION: (1)..(153)

<400> SEQUENCE: 16 gaa cgg gct aag atc aac ttg ctt cca aag aga aag cca cct gct gag      48
Glu Arg Ala Lys Ile Asn Leu Leu Pro Lys Arg Lys Pro Pro Ala Glu
 1               5                  10                  15 cgt tgg ttg gaa tgc agt gtt tgg ttt tca cat tgt acg aag gac tcg      96
Arg Trp Leu Glu Cys Ser Val Trp Phe Ser His Cys Thr Lys Asp Ser
            20                  25                  30 gaa tgt tgt tct aat agt tgt gac caa acg tac tgc acg tta atg cca     144
Glu Cys Cys Ser Asn Ser Cys Asp Gln Thr Tyr Cys Thr Leu Met Pro
        35                  40                  45 ccg gac tgg tgacatcgcc actctcctgt tcagagtctt caaggctttt             193
Pro Asp Trp
     50 gttctctttt gaagaatttt aacgagtgaa caaaaaagtg gactagcatg tttccttttc   253 cctttgcaaa atcaatgatg gaggtaaaag cctcccattt tgtcttcatc aataaagaac   313 ttatcatcat                                                          323

<210> SEQ ID NO 17
<211> LENGTH: 51
<212> TYPE: PRT
<213> ORGANISM: Conus textile

<400> SEQUENCE: 17

Glu Arg Ala Lys Ile Asn Leu Leu Pro Lys Arg Lys Pro Pro Ala Glu
 1               5                  10                  15

Arg Trp Leu Glu Cys Ser Val Trp Phe Ser His Cys Thr Lys Asp Ser
            20                  25                  30

Glu Cys Cys Ser Asn Ser Cys Asp Gln Thr Tyr Cys Thr Leu Met Pro
        35                  40                  45

Pro Asp Trp
     50

<210> SEQ ID NO 18
<211> LENGTH: 510
<212> TYPE: DNA
<213> ORGANISM: Conus textile
<220> FEATURE:

-continued

```
<221> NAME/KEY: CDS
<222> LOCATION: (95)..(337)

<400> SEQUENCE: 18
tgactcgcca tctcctctct cagtctccct gacagctgcc ttcagtcgac cctgccgtca        60
tctcaacgca cacttgaagt gaaaaacctt tatc atg gag aaa ctg aca att ctg       115
                                     Met Glu Lys Leu Thr Ile Leu
                                      1               5 ctt ctt gtt gct gct gta ctg ttg tcg atc cag gcc cta aat caa gaa         163
Leu Leu Val Ala Ala Val Leu Leu Ser Ile Gln Ala Leu Asn Gln Glu
         10                  15                  20 aaa cac caa cgg gca aag atc aac ttg ctt tca aag aga aag cca cct         211
Lys His Gln Arg Ala Lys Ile Asn Leu Leu Ser Lys Arg Lys Pro Pro
     25                  30                  35 gct gag cgt tgg tgg cgg tgg gga gga tgc atg gct tgg ttt ggg ctt         259
Ala Glu Arg Trp Trp Arg Trp Gly Gly Cys Met Ala Trp Phe Gly Leu
 40                  45                  50                  55 tgt tcg agg gac tcg gaa tgt tgt tct aat agt tgt gac gta acg cgc         307
Cys Ser Arg Asp Ser Glu Cys Cys Ser Asn Ser Cys Asp Val Thr Arg
                 60                  65                  70 tgc gag tta atg cca ttc cca cca gac tgg tgacatcgac actctcctct           357
Cys Glu Leu Met Pro Phe Pro Pro Asp Trp
             75                  80 tcagagtctt caaggctttt gttctctttt gaagaatttt tacgagtgaa caaaaacgtg        417
gactagcacg tttccttttc cctttgcaaa atcaatgatg gaggtaaaag tgtcccattt        477
tgtcttcatc aataaagaac ttatcatcat aat                                    510

<210> SEQ ID NO 19
<211> LENGTH: 81
<212> TYPE: PRT
<213> ORGANISM: Conus textile

<400> SEQUENCE: 19

Met Glu Lys Leu Thr Ile Leu Leu Val Ala Ala Val Leu Leu Ser
 1               5                  10                  15

Ile Gln Ala Leu Asn Gln Glu Lys His Gln Arg Ala Lys Ile Asn Leu
                 20                  25                  30

Leu Ser Lys Arg Lys Pro Pro Ala Glu Arg Trp Trp Arg Trp Gly Gly
             35                  40                  45

Cys Met Ala Trp Phe Gly Leu Cys Ser Arg Asp Ser Glu Cys Cys Ser
         50                  55                  60

Asn Ser Cys Asp Val Thr Arg Cys Glu Leu Met Pro Phe Pro Pro Asp
 65                  70                  75                  80

Trp

<210> SEQ ID NO 20
<211> LENGTH: 441
<212> TYPE: DNA
<213> ORGANISM: Conus textile
<220> FEATURE:
<221> NAME/KEY: CDS
<222> LOCATION: (16)..(243)

<400> SEQUENCE: 20
ggaaaaactt ttatc atg gag aaa ctg aca atc ctg ctc ctt gtt gct gct         51
                 Met Glu Lys Leu Thr Ile Leu Leu Leu Val Ala Ala
                  1               5                  10 gta ctg atg tcg acc cag gcc atg ttt caa ggt gat gga gaa aaa tcc         99
Val Leu Met Ser Thr Gln Ala Met Phe Gln Gly Asp Gly Glu Lys Ser
```

-continued

```
                       15                  20                  25
cgg aag gcg gag atc aac ttt tct gaa aca aga aag ttg gcg aga aac    147
Arg Lys Ala Glu Ile Asn Phe Ser Glu Thr Arg Lys Leu Ala Arg Asn
         30                  35                  40 aag cag aaa cgc tgc aaa act tat tca aag tat tgt gaa gct gac tcg    195
Lys Gln Lys Arg Cys Lys Thr Tyr Ser Lys Tyr Cys Glu Ala Asp Ser
 45                  50                  55                  60 gaa tgc tgt acc gaa cag tgt gta agg tct tac tgc acg ttg ttt gga    243
Glu Cys Cys Thr Glu Gln Cys Val Arg Ser Tyr Cys Thr Leu Phe Gly
                     65                  70                  75 tgaattcgga ccacaagcca tccgatatca cccctctcct cttcagaggc ttcaaggctt  303
ttgttatcct tttgaagaat ctttatcgag taaacataag tagacaagct ttttttttcc  363
tttgcaaaat gaagaatgat ggcaaaaagc ccccatttt gtcttcatca ataaagaact   423
cgctatcaga ataaaaaa                                                441

<210> SEQ ID NO 21
<211> LENGTH: 76
<212> TYPE: PRT
<213> ORGANISM: Conus textile

<400> SEQUENCE: 21

Met Glu Lys Leu Thr Ile Leu Leu Leu Val Ala Ala Val Leu Met Ser
 1               5                  10                  15

Thr Gln Ala Met Phe Gln Gly Asp Gly Glu Lys Ser Arg Lys Ala Glu
             20                  25                  30

Ile Asn Phe Ser Glu Thr Arg Lys Leu Ala Arg Asn Lys Gln Lys Arg
         35                  40                  45

Cys Lys Thr Tyr Ser Lys Tyr Cys Glu Ala Asp Ser Glu Cys Cys Thr
     50                  55                  60

Glu Gln Cys Val Arg Ser Tyr Cys Thr Leu Phe Gly
 65                  70                  75

<210> SEQ ID NO 22
<211> LENGTH: 460
<212> TYPE: DNA
<213> ORGANISM: Conus textile
<220> FEATURE:
<221> NAME/KEY: CDS
<222> LOCATION: (49)..(273)

<400> SEQUENCE: 22
ctgccgtcat ctcagcgcac acttggtaag aagtgaaaaa ccttgatc atg gag aaa    57
                                                    Met Glu Lys
                                                      1 ctg aca att ctg ctt ctt gtt gct gct gtg ctg atg tcg acc cag gcc    105
Leu Thr Ile Leu Leu Leu Val Ala Ala Val Leu Met Ser Thr Gln Ala
     5                  10                  15 cta att caa gat caa cgc caa aag gca aag atc aac ttg ttt tca aag    153
Leu Ile Gln Asp Gln Arg Gln Lys Ala Lys Ile Asn Leu Phe Ser Lys
 20                  25                  30                  35 aga cag gca tat gct cgt gat tgg tgg gac gat ggc tgc agt gtg tgg    201
Arg Gln Ala Tyr Ala Arg Asp Trp Trp Asp Asp Gly Cys Ser Val Trp
             40                  45                  50 ggg cct tgt acg gtg aac gca gaa tgt tgt tct ggt gat tgt cat gaa    249
Gly Pro Cys Thr Val Asn Ala Glu Cys Cys Ser Gly Asp Cys His Glu
         55                  60                  65 acg tgc att ttc ggg tgg gaa gtc tgaccacaaa ccatccgaca tcgccactct   303
Thr Cys Ile Phe Gly Trp Glu Val
     70                  75
```

```
cctcttcaga gacttcaagg cttttgttct cttttgaaga attttacgag tgagcaaaaa    363
ggtagactag cacgtttctt tttccctttg caaaatcaat gatggaggta aaagcctccc    423
attttgtcct catcaataaa gaacttatca tcataat                             460

<210> SEQ ID NO 23
<211> LENGTH: 75
<212> TYPE: PRT
<213> ORGANISM: Conus textile

<400> SEQUENCE: 23

Met Glu Lys Leu Thr Ile Leu Leu Leu Val Ala Ala Val Leu Met Ser
1               5                   10                  15

Thr Gln Ala Leu Ile Gln Asp Gln Arg Gln Lys Ala Lys Ile Asn Leu
            20                  25                  30

Phe Ser Lys Arg Gln Ala Tyr Ala Arg Asp Trp Trp Asp Asp Gly Cys
        35                  40                  45

Ser Val Trp Gly Pro Cys Thr Val Asn Ala Glu Cys Cys Ser Gly Asp
    50                  55                  60

Cys His Glu Thr Cys Ile Phe Gly Trp Glu Val
65                  70                  75

<210> SEQ ID NO 24
<211> LENGTH: 533
<212> TYPE: DNA
<213> ORGANISM: Conus textile
<220> FEATURE:
<221> NAME/KEY: CDS
<222> LOCATION: (110)..(337)

<400> SEQUENCE: 24
ctctgccggt tgacacntca tctactctct cagtctccct gacagctgcc ttcagtcgac     60
cctgccgtca tctcagcgca gacttgataa gaagtgaaaa acctttatc atg gag aaa    118
                                                      Met Glu Lys
                                                       1 ctg aca atc ctg ctt ctt gtt gct gct gta ctg atg tcg acc cag gcc      166
Leu Thr Ile Leu Leu Leu Val Ala Ala Val Leu Met Ser Thr Gln Ala
    5                   10                  15 ctg gtt gaa cgt gct gga gaa aac cac tca aag gag aac atc aat ttt      214
Leu Val Glu Arg Ala Gly Glu Asn His Ser Lys Glu Asn Ile Asn Phe
20                  25                  30                  35 tta tta aaa aga aag aga gct gct gac agg ggg atg tgg ggc gaa tgc      262
Leu Leu Lys Arg Lys Arg Ala Ala Asp Arg Gly Met Trp Gly Glu Cys
                40                  45                  50 aaa gat ggg tta acg aca tgt ttg gcg ccc tca gag tgt tgt tct gag      310
Lys Asp Gly Leu Thr Thr Cys Leu Ala Pro Ser Glu Cys Cys Ser Glu
            55                  60                  65 gat tgt gaa ggg agc tgc acg atg tgg tgatgaattc tgaccacaag             357
Asp Cys Glu Gly Ser Cys Thr Met Trp
        70                  75 ccatctgaca tcaccactct cctcttcaga ggcttcaagg cttttgtttt cctttttgaat   417 aatctttacg agtaaacaaa taagtagact agcgcgtttt tttccctttg agaaatcaat    477
gatggaggta aatagcttcc tattttgtct tattcaataa agaacttatc ataata        533

<210> SEQ ID NO 25
<211> LENGTH: 76
<212> TYPE: PRT
<213> ORGANISM: Conus textile
```

<400> SEQUENCE: 25

Met Glu Lys Leu Thr Ile Leu Leu Val Ala Ala Val Leu Met Ser
1               5                   10                  15

Thr Gln Ala Leu Val Glu Arg Ala Gly Glu Asn His Ser Lys Glu Asn
            20                  25                  30

Ile Asn Phe Leu Leu Lys Arg Lys Arg Ala Ala Asp Arg Gly Met Trp
            35                  40                  45

Gly Glu Cys Lys Asp Gly Leu Thr Thr Cys Leu Ala Pro Ser Glu Cys
50                  55                  60

Cys Ser Glu Asp Cys Glu Gly Ser Cys Thr Met Trp
65                  70                  75

<210> SEQ ID NO 26
<211> LENGTH: 408
<212> TYPE: DNA
<213> ORGANISM: Conus gloriamaris
<220> FEATURE:
<221> NAME/KEY: CDS
<222> LOCATION: (2)..(211)

<400> SEQUENCE: 26 g ctg aca atc ctg ctt ctt gtt gct gct gta ctg atg tcg acc cag gcc        49
  Leu Thr Ile Leu Leu Leu Val Ala Ala Val Leu Met Ser Thr Gln Ala
  1               5                   10                  15 ctg att caa ggt ggt ggt gac aaa cgt caa aag gca aac atc aac ttt          97
Leu Ile Gln Gly Gly Gly Asp Lys Arg Gln Lys Ala Asn Ile Asn Phe
            20                  25                  30 ctt tca agg tgg gac cgt gag tgc agg gct tgg tat gcg ccg tgt agc         145
Leu Ser Arg Trp Asp Arg Glu Cys Arg Ala Trp Tyr Ala Pro Cys Ser
        35                  40                  45 cct ggc gcg caa tgt tgt agt ttg ctg atg tgt tca aaa gcg acc agc         193
Pro Gly Ala Gln Cys Cys Ser Leu Leu Met Cys Ser Lys Ala Thr Ser
50                  55                  60 cgc tgc ata ttg gcg tta tgaactctga ccacaagcca tccgacatca                 241
Arg Cys Ile Leu Ala Leu
65                  70 ccactctcct cttcagaggc ttcaaggctt tttgttttc ttttgaagaa tctttacgag         301
tgaacaaata agtagaatag cacgttttc cccctttgca aaatcaataa tggaggttaa         361
aaaaaaactt ctgtcttctt caataaagaa gttatcataa taaaaaa                      408

<210> SEQ ID NO 27
<211> LENGTH: 70
<212> TYPE: PRT
<213> ORGANISM: Conus gloriamaris

<400> SEQUENCE: 27

Leu Thr Ile Leu Leu Leu Val Ala Ala Val Leu Met Ser Thr Gln Ala
1               5                   10                  15

Leu Ile Gln Gly Gly Gly Asp Lys Arg Gln Lys Ala Asn Ile Asn Phe
            20                  25                  30

Leu Ser Arg Trp Asp Arg Glu Cys Arg Ala Trp Tyr Ala Pro Cys Ser
        35                  40                  45

Pro Gly Ala Gln Cys Cys Ser Leu Leu Met Cys Ser Lys Ala Thr Ser
50                  55                  60

Arg Cys Ile Leu Ala Leu
65                  70

<210> SEQ ID NO 28

-continued

```
<211> LENGTH: 278
<212> TYPE: DNA
<213> ORGANISM: Conus marmoreus
<220> FEATURE:
<221> NAME/KEY: CDS
<222> LOCATION: (4)..(222)

<400> SEQUENCE: 28 atc atg cag aaa ctg ata atc ctg ctt ctt gtt gct gct gtg ctg ctg        48
    Met Gln Lys Leu Ile Ile Leu Leu Leu Val Ala Ala Val Leu Leu
     1               5                  10                  15 tcg acc cag gcc cta aat caa gaa aaa cgc cca aag gag atg atc aat        96
Ser Thr Gln Ala Leu Asn Gln Glu Lys Arg Pro Lys Glu Met Ile Asn
             20                  25                  30 ttt tta tca aaa gga aag aca aat gct gag agg cgg aac ggc caa tgc       144
Phe Leu Ser Lys Gly Lys Thr Asn Ala Glu Arg Arg Asn Gly Gln Cys
         35                  40                  45 gag gat gtt tgg atg cct tgt aca tcg aac tgg gaa tgc tgt tct ttg       192
Glu Asp Val Trp Met Pro Cys Thr Ser Asn Trp Glu Cys Cys Ser Leu
     50                  55                  60 gat tgt gaa atg tac tgc aca cag ata gga tgaactctga ccacaagcca         242
Asp Cys Glu Met Tyr Cys Thr Gln Ile Gly
 65                  70 tccgacatca ccactctcct cttcagagtc ttcaag                               278

<210> SEQ ID NO 29
<211> LENGTH: 73
<212> TYPE: PRT
<213> ORGANISM: Conus marmoreus

<400> SEQUENCE: 29

Met Gln Lys Leu Ile Ile Leu Leu Leu Val Ala Ala Val Leu Leu Ser
 1               5                  10                  15

Thr Gln Ala Leu Asn Gln Glu Lys Arg Pro Lys Glu Met Ile Asn Phe
             20                  25                  30

Leu Ser Lys Gly Lys Thr Asn Ala Glu Arg Arg Asn Gly Gln Cys Glu
         35                  40                  45

Asp Val Trp Met Pro Cys Thr Ser Asn Trp Glu Cys Cys Ser Leu Asp
     50                  55                  60

Cys Glu Met Tyr Cys Thr Gln Ile Gly
 65                  70

<210> SEQ ID NO 30
<211> LENGTH: 287
<212> TYPE: DNA
<213> ORGANISM: Conus marmoreus
<220> FEATURE:
<221> NAME/KEY: CDS
<222> LOCATION: (4)..(231)

<400> SEQUENCE: 30 atc atg gag aaa ctg aca atc ctg ctt ctt gtt gct gct gta ctg ata        48
    Met Glu Lys Leu Thr Ile Leu Leu Leu Val Ala Ala Val Leu Ile
     1               5                  10                  15 ccg acc cag gcc ctt ttt caa ggt gat gac gga aaa tcc cag aag gcg        96
Pro Thr Gln Ala Leu Phe Gln Gly Asp Asp Gly Lys Ser Gln Lys Ala
             20                  25                  30 gag atc aag tct ttt gaa aca aga aag tta gcg aga aac aag cag gta       144
Glu Ile Lys Ser Phe Glu Thr Arg Lys Leu Ala Arg Asn Lys Gln Val
         35                  40                  45 cgc tgc ggt ggt tgg tca acg tat tgt gaa gtt gac gag gaa tgc tgt       192
Arg Cys Gly Gly Trp Ser Thr Tyr Cys Glu Val Asp Glu Glu Cys Cys
```

-continued

```
              50                  55                  60
tcg gaa tca tgt gta agg tct tac tgc acg ctg ttt gga tgaactcgga         241
Ser Glu Ser Cys Val Arg Ser Tyr Cys Thr Leu Phe Gly
         65                  70                  75 ccacaagcca tccgatatca ccactctcct gttcagagtc ttcaag                     287
```

<210> SEQ ID NO 31
<211> LENGTH: 76
<212> TYPE: PRT
<213> ORGANISM: Conus marmoreus

<400> SEQUENCE: 31

Met Glu Lys Leu Thr Ile Leu Leu Val Ala Ala Val Leu Ile Pro
 1               5                  10                  15

Thr Gln Ala Leu Phe Gln Gly Asp Asp Gly Lys Ser Gln Lys Ala Glu
             20                  25                  30

Ile Lys Ser Phe Glu Thr Arg Lys Leu Ala Arg Asn Lys Gln Val Arg
         35                  40                  45

Cys Gly Gly Trp Ser Thr Tyr Cys Glu Val Asp Glu Glu Cys Cys Ser
     50                  55                  60

Glu Ser Cys Val Arg Ser Tyr Cys Thr Leu Phe Gly
 65                  70                  75

<210> SEQ ID NO 32
<211> LENGTH: 278
<212> TYPE: DNA
<213> ORGANISM: Conus marmoreus
<220> FEATURE:
<221> NAME/KEY: CDS
<222> LOCATION: (4)..(213)

<400> SEQUENCE: 32

```
atc atg cag aaa ctg ata att ctg ctt ctt gtt gct gct gtg ctg atg       48
    Met Gln Lys Leu Ile Ile Leu Leu Leu Val Ala Ala Val Leu Met
     1               5                  10                  15 acg acc cag gcc cta tat caa gaa aaa cgc cga aag gag atg atc aat       96
Thr Thr Gln Ala Leu Tyr Gln Glu Lys Arg Arg Lys Glu Met Ile Asn
             20                  25                  30 ttt tta tca aaa gga aag ata aat gct gag agg cgg aac ggc gga tgc      144
Phe Leu Ser Lys Gly Lys Ile Asn Ala Glu Arg Arg Asn Gly Gly Cys
         35                  40                  45 aaa gct act tgg atg tct tgt tca tcg ggc tgg gaa tgc tgt tct atg      192
Lys Ala Thr Trp Met Ser Cys Ser Ser Gly Trp Glu Cys Cys Ser Met
     50                  55                  60 agt tgt gac atg tac tgc gga tagataggat gaactctgac cacaagccat         243
Ser Cys Asp Met Tyr Cys Gly
 65                  70 ccgacatcac cactctcctc ttcagagtct tcaag                                278
```

<210> SEQ ID NO 33
<211> LENGTH: 70
<212> TYPE: PRT
<213> ORGANISM: Conus marmoreus

<400> SEQUENCE: 33

Met Gln Lys Leu Ile Ile Leu Leu Val Ala Ala Val Leu Met Thr
 1               5                  10                  15

Thr Gln Ala Leu Tyr Gln Glu Lys Arg Arg Lys Glu Met Ile Asn Phe
             20                  25                  30

Leu Ser Lys Gly Lys Ile Asn Ala Glu Arg Arg Asn Gly Gly Cys Lys

```
                 35                  40                    45

Ala Thr Trp Met Ser Cys Ser Ser Gly Trp Glu Cys Cys Ser Met Ser
        50                  55                  60

Cys Asp Met Tyr Cys Gly
65                  70

<210> SEQ ID NO 34
<211> LENGTH: 528
<212> TYPE: DNA
<213> ORGANISM: Conus textile
<220> FEATURE:
<221> NAME/KEY: CDS
<222> LOCATION: (98)..(316)

<400> SEQUENCE: 34
gcacgtcatc ttctctctca gtctgcctga cagctgcctt cagtcaaccc tgccgtcatc      60
tcagcgtaga cttggtaaga agtgaaaaac atttatc atg cag aaa ctg ata atc     115
                                        Met Gln Lys Leu Ile Ile
                                          1               5 ctg ctt ctt gtt gct gct gtg ctg atg tcg acc cag gcc gtg ctt caa      163
Leu Leu Leu Val Ala Ala Val Leu Met Ser Thr Gln Ala Val Leu Gln
         10                  15                  20 gaa aaa cgc cca aag gag aag atc aag ctt tta tca aag aga aag aca      211
Glu Lys Arg Pro Lys Glu Lys Ile Lys Leu Leu Ser Lys Arg Lys Thr
             25                  30                  35 gat gct gag aag cag cag aag cgc ctt tgc ccg gat tac acg gag cct      259
Asp Ala Glu Lys Gln Gln Lys Arg Leu Cys Pro Asp Tyr Thr Glu Pro
     40                  45                  50 tgt tca cat gcc cat gaa tgc tgt tca tgg aat tgt tat aat ggg cac      307
Cys Ser His Ala His Glu Cys Cys Ser Trp Asn Cys Tyr Asn Gly His
 55                  60                  65                  70 tgt acg gga tgaactcgga ccacaagcca tccgacatca ccactctcct              356
Cys Thr Gly cttcagaggc ttcaagactt tgttctgat ttggacaat ctttacgagt aaacaaataa      416
ttagactagc actttttttc cccttttgcaa atcaatgat ggaggtaaaa agcctcccat     476
tttgtcttca tcaataaaga acttatcatc aaaaaaaaaa aaaaaaaaa aa             528

<210> SEQ ID NO 35
<211> LENGTH: 73
<212> TYPE: PRT
<213> ORGANISM: Conus textile

<400> SEQUENCE: 35

Met Gln Lys Leu Ile Ile Leu Leu Leu Val Ala Ala Val Leu Met Ser
  1               5                  10                  15

Thr Gln Ala Val Leu Gln Glu Lys Arg Pro Lys Glu Lys Ile Lys Leu
             20                  25                  30

Leu Ser Lys Arg Lys Thr Asp Ala Glu Lys Gln Gln Lys Arg Leu Cys
         35                  40                  45

Pro Asp Tyr Thr Glu Pro Cys Ser His Ala His Glu Cys Cys Ser Trp
     50                  55                  60

Asn Cys Tyr Asn Gly His Cys Thr Gly
 65                  70

<210> SEQ ID NO 36
<211> LENGTH: 26
<212> TYPE: PRT
<213> ORGANISM: Conus textile
<220> FEATURE:
```

```
<221> NAME/KEY: PEPTIDE
<222> LOCATION: (1)..(26)
<223> OTHER INFORMATION: Xaa at residue 18 is Trp or 6-bromo-Trp; Xaa at
      residues 7 and 14 are Glu or gamma-carboxyglutamate; Xaa at
      residues 3 and 8 are Pro or hydroxy-Pro.

<400> SEQUENCE: 36

Leu Cys Xaa Asp Tyr Thr Xaa Xaa Cys Ser His Ala His Xaa Cys Cys
  1               5                  10                  15

Ser Xaa Asn Cys Tyr Asn Gly His Cys Thr
             20                  25

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence:consensus
      gamma-conopeptide sequence for probe
<220> FEATURE:
<221> NAME/KEY: PEPTIDE
<222> LOCATION: (1)
<223> OTHER INFORMATION: Xaa is Glu or Gln.

<400> SEQUENCE: 37

Xaa Cys Cys Ser
  1

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence:degenerate
      probe for consensus gamma-conopeptide sequence.

<400> SEQUENCE: 38
sartgytgya gy                                                          12

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence:degenerate
      probe for consensus gamma-conopeptide sequence.

<400> SEQUENCE: 39
sartgytgyt cn                                                          12

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence:consensus
      pro-gamma-conopeptide sequence for probe.

<400> SEQUENCE: 40

Ile Leu Leu Val Ala Ala Val Leu
  1               5

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:degenerate
``` probe for consensus pro-gamma-conopeptide sequence.

<400> SEQUENCE: 41
athytnytng tngcngcngt nytn 24

<210> SEQ ID NO 42
<211> LENGTH: 32
<212> TYPE: PRT
<213> ORGANISM: Conus pennaceus
<220> FEATURE:
<221> NAME/KEY: PEPTIDE
<222> LOCATION: (1)..(31)
<223> OTHER INFORMATION: Xaa at residues 14 and 26 are gamma-carboxyglutamate; Xaa at residue 31 is hdroxy-Pro.

<400> SEQUENCE: 42

```
Asp Cys Thr Ser Trp Phe Gly Arg Cys Thr Val Asn Ser Xaa Cys Cys
  1               5                  10                  15

Ser Asn Ser Cys Asp Gln Thr Tyr Cys Xaa Leu Tyr Ala Phe Xaa Ser
             20                  25                  30
```

<210> SEQ ID NO 43
<211> LENGTH: 27
<212> TYPE: PRT
<213> ORGANISM: Conus textile
<220> FEATURE:
<221> NAME/KEY: PEPTIDE
<222> LOCATION: (1)..(27)
<223> OTHER INFORMATION: Xaa at residues 9 and 13 are gamma-carboxyglutamate.

<400> SEQUENCE: 43

```
Cys Gly Gly Tyr Ser Thr Tyr Cys Xaa Val Asp Ser Xaa Cys Cys Ser
  1               5                  10                  15

Asp Asn Cys Val Arg Ser Tyr Cys Thr Leu Phe
             20                  25
```

<210> SEQ ID NO 44
<211> LENGTH: 8
<212> TYPE: PRT
<213> ORGANISM: Conus pennaceus
<220> FEATURE:
<221> NAME/KEY: MOD_RES
<222> LOCATION: (2)
<223> OTHER INFORMATION: Xaa at residue 2 is carboxymethylCys

<400> SEQUENCE: 44

```
Asp Xaa Thr Ser Trp Phe Gly Arg
  1               5
```

<210> SEQ ID NO 45
<211> LENGTH: 24
<212> TYPE: PRT
<213> ORGANISM: Conus pennaceus
<220> FEATURE:
<221> NAME/KEY: PEPTIDE
<222> LOCATION: (1)..(24)
<223> OTHER INFORMATION: Xaa at residues 6 and 18 are gamma-carboxyglutamate; Xaa at residue 23 is hydroxy-Pro.

<400> SEQUENCE: 45

```
Xaa Thr Val Asn Ser Xaa Xaa Xaa Ser Asn Ser Xaa Asp Gln Thr Tyr
  1               5                  10                  15

Xaa Xaa Leu Tyr Ala Phe Xaa Ser
             20
```

-continued

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:primer for M13 universal priming site.

<400> SEQUENCE: 46
tttcccagtc acgacgtt 18

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence:primer for M13 reverse priming site.

<400> SEQUENCE: 47
cacacaggaa acagctatg 19

US 6,624,288 B1

GAMMA-CONOPEPTIDES

CROSS-REFERENCE TO RELATED APPLICATION

The present application claims benefit to U.S. provisional patent application Serial No. 60/069,706, filed Dec. 16, 1997, incorporated herein by reference.

This invention was made in part with Government support under Grant No. RR01614 and GM48677 awarded by the National Institutes of Health, Bethesda, Md. and under Grant No. DIR8700766 awarded by the National Science Foundation, Washington, D.C. The United States Government has certain rights in the invention.

BACKGROUND OF THE INVENTION

This invention relates to relatively short peptides about 25–40 residues in length, which are naturally available in minute amounts in the venom of the cone snails or analogs to the naturally available peptides, and which include three cyclizing disulfide linkages and one or more γ-carboxyglutamate residues.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. Many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used, however, every Conus species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). A conotoxin, TxVIIA, containing a γ-carboxyglutamate residue and three disulfide bonds has been isolated (Fainzilber et al., 1991). Conopressins, which are vasopressin analogs, have also been identified (Cruz et al., 1987). In addition, peptides named conantokins have been isolated from Conus geographus and *Conus tulipa* (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990). Recently, peptides named contryphans containing D-tryptophan or D-leucine residues have been isolated from Conus radiatus (U.S. Ser. No. 09/061,026), and bromotryptophan conopeptides have been isolated from *Conus imperialis* and *Conus radiatus* (U.S. Ser. No. 08/785,534).

Ion channels are integral plasma membrane proteins responsible for electrical activity in excitable tissues. It has been recognized that slow inward currents can influence neuronal excitability via long-lasting depolarizations of the cell membrane (Llinás, 1988). The role of slow inward currents in generating endogenous bursting behavior has been recognized in molluscan neurons (Wilson & Wachtel, 1974; Eckert & Lux, 1976; Partridge et al., 1979), and more recently in some types of mammalian neurons (Lanthorn et al., 1984; Stafstrom et al., 1985; Llinàs, 1988; Alonso & Llinàs, 1989). Changes in the slow inward currents carried by such nonspecific cation channels may play a crucial role in bursting and pacemaker activities in a variety of excitable systems, ranging from mammalian heart muscle to molluscan neurons (Partridge & Swandulla, 1988; Hoehn et al., 1993; Kits & Mansvelder, 1966; van Soest & Kits, 1997). Slow inward currents are also believed to be important in generating epileptiform bursting in regions of the brain such as the hippocampus.

It is desired to identify drugs which are useful for modulating slow inward cation channels in vertebrates involved in syndromes of clinical relevance, such as epileptic activity in hippocampus (Hoehn et al., 1993) and pacemaker potentials in heart muscle (Reuter, 1984).

SUMMARY OF THE INVENTION

This invention relates to relatively short peptides about 25–40 residues in length, which are naturally available in minute amounts in the venom of the cone snails or analogs to the naturally available peptides, and which include three cyclizing disulfide linkages and one or more γ-carboxyglutamate residues.

More specifically, the present invention is directed to conopeptides having the general formula I:

Xaa$_1$-Xaa$_1$-Xaa$_1$-Xaa$_1$-Xaa$_1$-Xaa$_1$-Cys-Xaa$_2$-Xaa$_2$-Xaa$_2$-Xaa$_2$-Xaa$_2$-Xaa$_3$-Cys-Xaa$_2$-Xaa$_2$-Xaa$_2$-Xaa$_2$-Xaa$_4$-Cys-Cys-Xaa$_5$-Xaa$_6$-Xaa$_7$-Xaa$_8$-Cys-Xaa$_2$-Xaa$_2$-Xaa$_2$-Xaa$_3$-Xaa$_3$-Xaa$_3$-Cys-Xaa$_9$-Xaa$_9$-Xaa$_{10}$-Xaa$_{10}$-Xaa$_{10}$-Xaa$_{10}$-Xaa$_{10}$-Xaa$_{10}$-Xaa$_{10}$ (SEQ ID NO: 1), wherein Xaa$_1$ is des-Xaa$_1$ or any amino acid; Xaa$_2$ is any amino acid; Xaa$_3$ is des-Xaa$_3$ or any amino acid; Xaa$_4$ is Glu γ-Glu (γ-carboxyglutamic acid; also referred to as Gla) or Gln; Xaa$_5$ is any amino acid; Xaa$_6$ is any amino acid; Xaa$_7$ is any amino acid; Xaa$_8$ is des-Xaa$_8$ or any amino acid; Xaa$_9$ is des-Xaa$_9$ or any amino acid; and Xaa$_{10}$ is des-Xaa$_{10}$ or any amino acid, with the provisos that (a) when all Xaa$_{10}$ are des-Xaa$_{10}$, then both Xaa$_9$ are des-Xaa$_9$ or any amino acid and (b) when all Xaa$_1$ are des-Xaa$_1$, then Xaa$_5$-Xaa$_6$-Xaa$_7$-Xaa$_8$- is not Ser-Asp-Asn.

general formula II:

Xaa$_1$-Xaa$_1$-Xaa$_1$-Xaa$_1$-Xaa$_1$-Xaa$_1$-Cys-Xaa$_2$-Xaa$_2$-Xaa$_2$-Xaa$_2$-Xaa$_2$-Xaa$_2$-Xaa$_3$-Cys-Xaa$_2$-Xaa$_2$-Xaa$_2$-Xaa$_2$-

Xaa$_4$-Cys-Cys-Xaa$_5$-Xaa$_6$-Xaa$_7$-Xaa$_8$-Cys-Xaa$_2$-Xaa$_2$-Xaa$_2$-Xaa$_3$-Xaa$_3$-Xaa$_3$-Cys-Xaa$_9$-Xaa$_9$-Xaa$_{10}$-Xaa$_{10}$-Xaa$_{10}$-Xaa$_{10}$-Xaa$_{10}$-Xaa$_{10}$-Xaa$_{10}$ (SEQ ID NO:2), wherein Xaa$_1$ is des-Xaa$_1$ or any amino acid; Xaa$_2$ is any amino acid; Xaa$_3$ is des-Xaa$_3$ or any amino acid; Xaa$_4$ is Glu, γ-Glu or Gln; Xaa$_5$ is Ser or Thr; Xaa$_6$ is any amino acid; Xaa$_7$ is any amino acid; Xaa$_8$ is des-Xaa$_8$ or any amino acid; Xaa$_9$ is des-Xaa$_9$ or any amino acid; and Xaa$_{10}$ is des-Xaa$_{10}$ or any amino acid, with the provisos that (a) when all Xaa$_{10}$ are des-Xaa$_{10}$, then both Xaa$_9$ are des-Xaa$_9$ or any amino acid and (b) when all Xaa$_1$ are des-Xaa$_1$ and Xaa$_5$ is Ser, then Xaa$_6$-Xaa$_7$-Xaa$_8$- is not Asp-Asn.

general formula III:

Xaa$_1$-Xaa$_2$-Xaa$_2$-Xaa$_2$-Xaa$_2$-Xaa$_2$-Cys-Xaa$_1$-Xaa$_1$-Xaa$_1$-Xaa$_1$-Xaa$_1$-Xaa$_1$-Cys-Xaa$_1$-Xaa$_1$-Xaa$_1$-Xaa$_1$-Xaa$_3$-Cys-Cys-Ser-Asn-Ser-Cys-Asp-Xaa$_1$-Xaa$_1$-Xaa$_1$-Cys-Xaa$_1$-Xaa$_1$-Xaa$_1$-Xaa$_1$-Xaa$_1$-Xaa$_1$-Xaa$_1$-Xaa$_2$-Xaa$_2$ (SEQ ID NO:3), wherein Xaa$_1$ is any amino acid; Xaa$_2$ is des-Xaa$_2$ or any amino acid and Xaa$_3$ is Glu or γ-Glu.

general formula IV:

Xaa$_1$-Xaa$_2$-Xaa$_2$-Xaa$_2$-Xaa$_2$-Xaa$_2$-Cys-Xaa$_1$-Xaa$_1$-Xaa$_1$-Xaa$_1$-Xaa$_1$-Xaa$_1$-Cys-Xaa$_3$-Xaa$_1$-Xaa$_1$-Xaa$_1$-Xaa$_4$-Cys-Cys-Ser-Asn-Ser-Cys-Asp-Xaa$_1$-Xaa$_1$-Xaa$_1$-Cys-Xaa$_1$-Xaa$_1$-Xaa$_1$-Xaa$_1$-Xaa$_1$-Xaa$_1$-Xaa$_1$-Xaa$_2$-Xaa$_2$ (SEQ ID NO:4), wherein Xaa$_1$ is any amino acid; Xaa$_2$ is des-Xaa$_2$ or any amino acid; Xaa$_3$ is Ser or Thr; and Xaa$_4$ is Glu or γ-Glu.

or general formula V:

Xaa$_1$-Xaa$_1$-Xaa$_2$-Cys-Xaa$_3$-Xaa$_3$-Xaa$_4$-Phe-Xaa$_3$-Xaa$_3$-Cys-Thr-Xaa$_3$-Xaa$_3$-Ser-Xaa$_5$-Cys-Cys-Ser-Asn-Ser-Cys-Asp-Gln-Thr-Tyr-Cys-Xaa$_3$-Leu-Xaa$_3$-Xaa$_3$-Xaa$_3$-Xaa$_3$-Xaa$_3$ (SEQ ID NO:5), wherein Xaa$_1$ is des-Xaa$_1$ or any amino acid; Xaa$_2$ is Asp, Glu or γ-Glu; Xaa$_3$ is any amino acid; Xaa$_4$ is Trp or 6-bromo-Trp; and Xaa$_5$ is Glu or γ-Glu.

The amino acid or the amino acid residues of the peptides is an amino acid selected from the group consisting of natural, modified or non-natural amino acids. The disulfide bridges in the conopeptides of general formulas I–V (as well as the specific conopeptides described herein) are between the first and fourth cysteine residues, between the second and fifth cysteine residues and between the third and sixth cysteine residues. The C-terminal end may contain a carboxyl or amide group. The invention also includes pharmaceutically acceptable salts of the conopeptides. These conopeptides are useful for modulating slow inward cation channels in vertebrates involved in syndromes of clinical relevance, such as epileptic activity in hippocampus (Hoehn et al., 1993) and pacemaker potentials in heart muscle (Reuter, 1984). Thus, the conopeptides are useful as agonists of neuronal pacemaker cation channels.

The invention further relates to the specific peptides:

Asp-Cys-Thr-Ser-Xaa$_1$-Phe-Gly-Arg-Cys-Thr-Val-Asn-Ser-Xaa$_2$-Cys-Cys-Ser-Asn-Ser-Cys-Asp-Gln-Thr-Tyr-Cys-Xaa$_2$-Leu-Tyr-Ala-Phe-Xaa$_3$-Ser (SEQ ID NO:6) (PnVIIA), wherein Xaa$_1$ is Trp or 6-bromo-Trp; Xaa$_2$ is Glu or γ-Glu, preferably γ-Glu; Xaa$_3$ is Pro or hydroxy-Pro (Hyp), preferably Hyp; and the C-terminus is a free carboxyl group or is amidated, preferably a free carboxyl group;

Xaa$_1$-Leu-Xaa$_2$-Cys-Ser-Val-Xaa$_1$-Phe-Ser-His-Cys-Thr-Lys-Asp-Ser-Xaa$_2$-Cys-Cys-Ser-Asn-Ser-Cys-Asp-Gln-Thr-Tyr-Cys-Thr-Leu-Met-Xaa$_3$-Xaa$_3$-Asp-Xaa$_1$ (SEQ ID NO:7) (Tx6.4), wherein Xaa$_1$ is Trp or 6-bromo-Trp; Xaa$_2$ is Glu or γ-Glu, preferably γ-Glu; Xaa$_3$ is Pro or Hyp, preferably Hyp; and the C-terminus is a free carboxyl group or is amidated, preferably a free carboxyl group;

Xaa$_1$-Xaa$_1$-Arg-Xaa$_1$-Gly-Gly-Cys-Met-Ala-Xaa$_1$-Phe-Gly-Leu-Cys-Ser-Arg-Asp-Ser-Xaa$_2$-Cys-Cys-Ser-Asn-Ser-Cys-Asp-Val-Thr-Arg-Cys-Xaa$_2$-Leu-Met-Xaa$_3$-Phe-Xaa$_3$-Xaa$_3$-Asp-Xaa$_1$ (SEQ ID NO:8) (Tx6.9), wherein Xaa$_1$ is Trp or 6-bromo-Trp; Xaa$_2$ is Glu or γ-Glu, preferably γ-Glu; Xaa$_3$ is Pro or Hyp, preferably Hyp; and the C-terminus is a free carboxyl group or is amidated, preferably a free carboxyl group;

Cys-Lys-Thr-Tyr-Ser-Lys-Tyr-Cys-Xaa$_2$-Ala-Asp-Ser-Xaa$_2$-Cys-Cys-Thr-Xaa$_2$-Gln-Cys-Val-Arg-Ser-Tyr-Cys-Thr-Leu-Phe (SEQ ID NO:9) (J010), wherein Xaa$_2$ is Glu or γ-Glu, preferably γ-Glu; and the C-terminus is a free carboxyl group or is amidated, preferably amidated;

Asp-Xaa$_1$-Xaa$_1$-Asp-Asp-Gly-Cys-Ser-Val-Xaa$_1$-Gly-Xaa$_3$-Cys-Thr-Val-Asn-Ala-Xaa$_2$-Cys-Cys-Ser-Gly-Asp-Cys-His-Xaa$_2$-Thr-Cys-Ile-Phe-Gly-Xaa$_3$-Xaa$_2$-Val (SEQ ID NO:10) (Tx6.6), wherein Xaa$_1$ is Trp or 6-bromo-Trp; Xaa$_2$ is Glu or γ-Glu, preferably γ-Glu; Xaa$_3$ is Pro or Hyp, preferably Hyp; and the C-terminus is a free carboxyl group or is amidated, preferably a free carboxyl group;

Gly-Met-Xaa$_1$-Gly-Xaa$_2$-Cys-Lys-Asp-Gly-Leu-Thr-Thr-Cys-Leu-Ala-Xaa$_3$-Ser-Xaa$_2$-Cys-Cys-Ser-Xaa$_2$-Asp-Cys-Xaa$_2$-Gly-Ser-Cys-Thr-Met-Xaa$_1$(SEQ ID NO:11) (Tx6.5), wherein Xaa$_1$ is Trp or 6-bromo-Trp; Xaa$_2$ is Glu or γ-Glu, preferably γ-Glu; Xaa$_3$ is Pro or Hyp, preferably Hyp; and the C-terminus is a free carboxyl group or is amidated, preferably a free carboxyl group;

Xaa$_2$-Cys-Arg-Ala-Xaa$_1$-Tyr-Ala-Xaa$_3$-Cys-Ser-Xaa$_3$-Gly-Ala-Gln-Cys-Cys-Ser-Leu-Leu-Met-Cys-Ser-Lys-Ala-Thr-Ser-Arg-Cys-Ile-Leu-Ala-Leu (SEQ ID NO:12) (Gm6.7), wherein Xaa$_1$ is Trp or 6-bromo-Trp; Xaa$_2$ is Glu or γ-Glu, preferably γ-Glu; Xaa$_3$ is Pro or Hyp, preferably Hyp; and the C-terminus is a free carboxyl group or is amidated, preferably a free carboxyl group;

Asn-Gly-Gln-Cys-Xaa$_2$-Asp-Val-Xaa$_1$-Met-Xaa$_3$-Cys-Thr-Ser-Asn-Xaa$_1$-Xaa$_2$-Cys-Cys-Ser-Leu-Asp-Cys-Xaa$_2$-Met-Tyr-Cys-Thr-Gln-Ile (SEQ ID NO:13) (Mr6.1), wherein Xaa$_1$ is Trp or 6-bromo-Trp; Xaa$_2$ is Glu or γ-Glu, preferably γ-Glu; Xaa$_3$ is Pro or Hyp, preferably Hyp; and the C-terminus is a free carboxyl group or is amidated, preferably amidated;

Cys-Gly-Gly-Xaa$_1$-Ser-Thr-Tyr-Cys-Xaa$_2$-Val-Asp-Xaa$_2$-Xaa$_2$-Cys-Cys-Ser-Xaa$_2$-Ser-Cys-Val-Arg-Ser-Tyr-Cys-Thr-Leu-Phe (SEQ ID NO:14) (Mr6.2), wherein Xaa$_1$ is Trp or 6-bromo-Trp; Xaa$_2$ is Glu or γ-Glu, preferably γ-Glu; and the C-terminus is a free carboxyl group or is amidated, preferably amidated;

Asn-Gly-Gly-Cys-Lys-Ala-Thr-Xaa$_1$-Met-Ser-Cys-Ser-Ser-Gly-Xaa$_1$-Xaa$_2$-Cys-Cys-Ser-Met-Ser-Cys-Asp-Met-Try-Cys (SEQ ID NO:15) (Mr6.3), wherein Xaa$_1$ is Trp or 6-bromo-Trp; Xaa$_2$ is Glu or γ-Glu, preferably γ-Glu; and the C-terminus is a free carboxyl group or is amidated, preferably amidated.

Finally, the invention further relates to the propeptide sequences for the above peptides and the DNA sequences coding for these propeptide sequences as described in further detail herein.

SEQUENCE SUMMARY

SEQ ID NO:1=γ-conopeptides of general formula I; SEQ ID NO:2=γ-conopeptides of general formula II; SEQ ID NO:3=γ-conopeptides of general formula III; SEQ ID NO:4=γ-conopeptides of general formula IV; SEQ ID NO:5=γ-conopeptides of general formula V; SEQ ID NO:6=γ-conopeptide corresponding to PnVIIA; SEQ ID NO:7=γ-conopeptide corresponding to Tx6.4; SEQ ID NO:8=γ-conopeptide corresponding to Tx6.9; SEQ ID NO:9=γ-conopeptide corresponding to J010; SEQ ID NO:10=γ-conopeptide corresponding to Tx6.6; SEQ ID NO:11=γ-conopeptide corresponding to Tx6.5; SEQ ID NO:12=γ-conopeptide corresponding to Gm6.7; SEQ ID NO:13=γ-conopeptide corresponding to Mr6.1; SEQ ID NO:14=γ-conopeptide corresponding to Mr6.2; SEQ ID NO:15=γ-conopeptide corresponding to Mr6.3; SEQ ID NO:16=DNA encoding propeptide of Tx6.4; SEQ ID NO:17=propeptide of Tx6.4; SEQ ID NO:18=DNA encoding propeptide of Tx6.9; SEQ ID NO:19=propeptide of Tx6.9; SEQ ID NO:20=DNA encoding propeptide of J010; SEQ ID NO:21= propeptide of J010; SEQ ID NO:22=DNA encoding propeptide of Tx6.6; SEQ ID NO:23=propeptide of Tx6.6; SEQ ID NO:24=DNA encoding propeptide of Tx6.5; SEQ ID NO:25=propeptide of Tx6.5; SEQ ID NO:26=DNA encoding propeptide of Gm6.7; SEQ ID NO:27=propeptide of Gm6.7; SEQ ID NO:28=DNA encoding propeptide of Mr6.1; SEQ ID NO:29=propeptide of Mr6.1; SEQ ID NO:30= DNA encoding propeptide of Mr6.2; SEQ ID NO:31= propeptide of Mr6.2; SEQ ID NO:32=DNA encoding propeptide of Mr6.3; SEQ ID NO:33=propeptide of Mr6.3; SEQ ID NO:34=DNA encoding propeptide of Tx6.1; SEQ ID NO:35=propeptide of Tx6.1; SEQ ID NO:36=γ-conopeptide corresponding to Tx6.1; SEQ ID NO:37= consensus sequence of γ-conopeptides PnVIIA and Tx6.4; SEQ ID NO:38=degenerate probe for consensus sequence of γ-conopeptides; SEQ ID NO:39=degenerate probe for consensus sequence of γ-conopeptides; SEQ ID NO:40= consensus sequence of pro-γ-conopeptides; SEQ ID NO:41= degenerate probe for consensus sequence of pro-γ-conopeptides; SEQ ID NO:42=γ-conopeptide PnVIIA; SEQ ID NO:43=γ-conopeptide TxVIIA; SEQ ID NO:44=N-terminal tryptic peptide of γ-conopeptide PnVIIA; SEQ ID NO:45=C-terminal tryptic peptide of γ-conopeptide PnVIIA; SEQ ID NO:46=primer for isolating conopeptides from Conus textile cDNA library; SEQ ID NO:47=primer for isolating conopeptides from Conus textile cDNA library.

DETAILED DESCRIPTION OF THE PREFERRED EMBODIMENT

This invention relates to relatively short peptides about 25–40 residues in length, which are naturally available in minute amounts in the venom of the cone snails or analogs to the naturally available peptides, and which include three cyclizing disulfide linkages and one or more γ-carboxyglutamate residues.

More specifically, the present invention is directed to conopeptides having the general formulas I–V described above. The invention is also directed to the specific γ-conopeptides PnVIIA, Tx6.4, Tx6.9, J010, Tx6.6, Tx6.5, Gm6.7, Mr6.1, Mr6.2 and Mr6.3, the sequences of which are described above.

The invention is further directed to isolated nucleic acids which encode γ-conopeptides, including the above and γ-conopeptide Tx6.1, and to isolated propeptides encoded by the nucleic acids. This aspect of the present invention is set forth in Table 1.

TABLE 1

Nucleic Acids and Propeptides of γ-Conopeptides

| γ-Conopeptide | Nucleic Acid SEQ ID NO: | Propeptide SEQ ID NO: |
| --- | --- | --- |
| Tx6.4 | 16 | 17 |
| Tx6.9 | 18 | 19 |
| J010 | 20 | 21 |
| Tx6.6 | 22 | 23 |
| Tx6.5 | 24 | 25 |
| Gm6.7 | 26 | 27 |
| Mr6.1 | 28 | 29 |
| Mr6.2 | 30 | 31 |
| Mr6.3 | 32 | 33 |
| Tx6.1 | 34 | 35 |

The mature peptide sequence for Tx6.1 is LCX$_3$DYTX$_2$X$_3$CSHAHX$_2$CCSX$_1$NCYNGHCT (SEQ ID NO:36), wherein X$_1$, X$_2$ and X$_3$ are as described for Xaa $_{,1}$Xaa $_2$and Xaa, $_3$ respectively. The C-terminus is preferably amidated.

The conopeptides of the present invention are useful for modulating slow inward cation channels in vertebrates involved in syndromes of clinical relevance, such as epileptic activity in hippocampus (Hoehn et al., 1993) and pacemaker potentials in heart muscle (Reuter, 1984). Thus, the conopeptides are useful as agonists of neuronal pacemaker cation channels.

The γ-conopeptides of the present invention are identified by isolation from Conus venom. Alternatively, the γ-conopeptides of the present invention are identified using recombinant DNA techniques. According to this method of identification, cDNA libraries of various Conus species are screened using conventional techniques with degenerate probes for the peptide consensus sequence Xaa-Cys-Cys-Ser (SEQ ID NO:37), wherein Xaa is Glu or Gln. Suitable probes are 5' SARTGYTGYAGY 3' (SEQ ID NO:38) or 5' SARTGYTGYTCN 3' (SEQ ID NO:39). Alternatively, cDNA libraries are screened with degenerate probes for the propeptide consensus sequence Ile-Leu-Leu-Val-Ala-Ala-Val-Leu (SEQ ID NO:40). Suitable probes for this sequence are 5' ATHYTNYTNGTNGCNGCNGTNYTN 3' (SEQ ID NO:4 1). Clones which hybridize to these probes are analyzed to identify those which meet minimal size requirements, i.e., clones having approximately 300 nucleotides (for a propeptide), as determined using PCR primers which flank the cDNA cloning sites for the specific cDNA library being examined. These minimal-sized clones are then sequenced. The sequences are then examined for the presence of a peptide having the characteristics noted above for γ-conopeptides, such as the presence of a Glu residue which could be modified to a γ-Glu and 6 cysteine residues. The biological activity of the peptides identified by this method is tested as described herein.

These peptides are sufficiently small to be chemically synthesized. General chemical syntheses for preparing the foregoing conopeptides peptides are described hereinafter, along with specific chemical synthesis of conopeptides and indications of biological activities of these synthetic products. Various ones of these conopeptides can also be obtained by isolation and purification from specific Conus species using the techniques described in U.S. Pat. No. 4,447,356 (Olivera et al., 1984), U.S. Pat. No. 5,514,774 (Olivera et al., 1996) and U.S. Pat. No. 5,591,821 (Olivera et al., 1997), the disclosures of which are incorporated herein by reference.

Although the conopeptides of the present invention can be obtained by purification from cone snails, because the amounts of conopeptides obtainable from individual snails are very small, the desired substantially pure conopeptides are best practically obtained in commercially valuable amounts by chemical synthesis using solid-phase strategy. For example, the yield from a single cone snail may be about 10 micrograms or less of conopeptide. By "substantially pure" is meant that the peptide is present in the substantial absence of other biological molecules of the same type; it is preferably present in an amount of at least about 85% purity and preferably at least about 95% purity. Chemical synthesis of biologically active conopeptides depends of course upon correct determination of the amino acid sequence. Thus, the conopeptides of the present invention may be isolated, synthesized and/or substantially pure.

The conopeptides can also be produced by recombinant DNA techniques well known in the art. Such techniques are described by Sambrook et al. (1979). The peptides produced in this manner are isolated, reduced if necessary, and oxidized to form the correct disulfide bonds, if present in the final molecule.

One method of forming disulfide bonds in the conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conopeptide molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. 29 (1987), Nishiuchi et al. (1993) and Zhou et al. (1996).

Synthesis of conopeptides have been described in U.S. Pat. No. 4,447,356 (Olivera et al., 1984), U.S. Pat. No. 5,514,774 (Olivera et al., 1996) and U.S. Pat. No. 5,591,821 (Olivera et al., 1997).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or param-ethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder and Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder and Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above. A suitable method for cyclization is the method described by Cartier et al. (1996).

The present γ-conotoxins are useful for modulating slow inward cation channels in 1:57, vertebrates involved in syndromes of clinical relevance, such as epileptic activity in hippocampus (Hoehn et al., 1993) and pacemaker potentials in heart muscle (Reuter, 1984). Thus, the conopeptides are useful as agonists of neuronal pacemaker cation channels.

Pharmaceutical compositions containing a compound of the present invention as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The conopeptides are administered in an amount sufficient to agonize the neuronal pacemaker calcium channels. The dosage range at which the conopeptides exhibit this agonistic effect can vary widely depending upon the particular condition being treated, the severity of the patient's condition, the patient, the specific conopeptide being administered, the route of administration and the presence of other underlying disease states within the patient. Typically, the conopeptides of the present invention exhibit their therapeutic effect at a dosage range from about 0.05 mg/kg to about 250 mg/kg, and preferably from about 0.1 mg/kg to about 100 mg/kg of the active ingredient. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved.

EXAMPLES

The present invention is described by reference to the following Examples, which are offered by way of illustration and are not intended to limit the invention in any manner. Standard techniques well known in the art or the techniques specifically described below were utilized.

Example 1

Experimental Procedures

Toxins and Bioassays. Venom of *Conus pennaceus* was obtained from specimens collected in the Northern Red Sea. Conotoxin-TxVIIA was from venom-purified aliquots (Fainzilber et al., 1991). Assays for paralysis in limpet snails (*Patella caerulea*), bivalves (*Mytilus edulis*), and fish (*Gambusia affinis*) were performed as previously described (Fainzilber et al., 1995).

Column Chromatography. *Conus pennaceus* venom was extracted and fractionated on Sephadex G-50 (Pharmacia) and semipreparative C18 (Vydac) columns as previously described (Fainzilber et al., 1994). Final purification of the active peptides was on wide pore reverse-phase phenyl (Vydac, 25×0.46 cm, 0.5 µm particle size) as described in FIG. 1, with on-line spectral analysis of peak purity utilizing a Hewlett-Packard 1040A Diode Array Detector coupled with HP 300 Chemstation Software.

Amino Acid Analysis. Analysis of amino acid composition after acid hydrolysis and 9-fluorenylmethyl-oxycabonyl-chloride (FMOC) derivatization was performed on a Merck-Hitachi reverse-phase HPLC system, according to Betner & Foldi, 1988. The system was calibrated prior to each analysis with FMOC-amino acid standards.

Reduction and alkylation. Dried purified peptides were dissolved in 50 µl of 0.1M $NH_4HCO_3$ (pH 8) containing 6M guanidine-HCl and 10 µM EDTA, and reduced with 200 µg of D11 at 37° C. for 2 hrs under argon. 4 vinylpyridine, or iodoacetic acid, or iodoacetamide were added and the mixture incubated at 37° C. for 1.5 hrs under argon. The alkylated peptide sample was purified on reverse-phase HPLC immediately after derivatization.

Edman Degradation Analyses. Reverse-phase purified peptides were applied to PVDF or glass fiber filters, and sequenced by automated Edman degradation on an Applied Biosystems 475A gas-phase protein sequencing system.

Proteolytic digest. HPLC purified sample of reduced and alkylated peptide was digested with TPCK-trypsin (Pierce, Rockford, Ill.) for 20 hrs at 37° C. A portion of the digest was directly analyzed by LCIESI/MS, and the remainder purified by reverse-phase HPLC. pH of the digest was adjusted to 3.0 prior to loading on the HPLC, in order to minimize the possibility of γ-carboxyglutamate decomposition in extremely acidic conditions. Purified C-terminal peptide fragments were further digested by Endoproteinase Asp-N (Boehringer-Mannheim, Indianapolis, Ind.) for 20 hrs at 37° C., and immediately purified on reverse-phase HPLC. A portion of the purified Asp N peptide was then methylated for LSI CID mass spectrometry.

Mass spectrometry. Microbore LC/ESI/MS experiments were carried out on a VG/Fisons (Manchester, U.K.) platform mass spectrometer using a C18 column (macrosphere C18, 5 µm particle size, 1×250 mm, Alitech, Deerfield Ill.) with a linear gradient of 2–62% acetonitrile in 0. 1% TFA in 60 min. A post column addition of make up solvent, 2-propanol/2-methoxyethanol (1:1) was used to optimize spraying and ionization performance (Medzihradszky et al., 1994). High energy CID mass spectra were obtained with a Kratos (Manchester, U.K.) Concept IIHH tandem mass spectrometer equipped with a continuous flow liquid secondary ionization source and a scanning charge-coupled device array detector (Burlingame, 1994).

Electrophysiology. Isolated Lymnaea caudodorsal neurons were kept in Petri dishes (Costar) and bathed in Hepes buffered saline (in mM: NaCl 30, $NaCH_3SO_4$ 10, $NaHCO_3$ 5, KCl 1.7, $CaCl_2$ 4, $MgCl_2$ 1.5, HEPES 10; pH 7.8 set with NaOH). To record calcium, sodium or potassium currents, HBS was replaced under continuous perfusion by the appropriate saline. The compositions of extracellular and pipette solutions used to selectively record specific currents were as follows (in 10 mM): Extracellular $I_{Ca}$ saline: TEACl 40, $CaCl_2$ 4, HEPES 10, 4aminopyridine 2, pH 7.8 set with TEAOH; Extracellular $I_{Na}$ saline: NaCl 47.5, $CaCl_2$ 4, $MgCl_2$ 1, HEPES 10, CdCl 0.1, 4-aminopyridine 1, pH 7.8 set with NaOH; Pipette saline ($I_{Ca}$ and $I_{Na}$): CsCl 29, $CaCl_2$ 2.3, HEPES 10, EGTA 11, ATPMg 2, GTPtris 0.1, pH 7.4 adjusted with CsOH; Pipette saline (non-selective): KCl 29, $CaCl_2$ 2.3, HEPES 10, EGTA 11, ATPMg 2, GTPtris 0.1, pH 7.4 adjusted with KOH. Toxin was administered by means of a laboratory-built pressure ejection system through a small glass pipette (tip diameter 20 µM) placed at ~100 µM from the recorded cell. This enabled rapid application of toxins, which were applied continuously during voltage ramps or series of depolarizing voltage steps.

Membrane potential measurements were performed using sharp microelectrodes filled with 0.5 M KCl (40 MΩ) using an Axoclamp 2A (Axon Instr., Foster City, Iowa) amplifier in the bridge balance mode. Whole-cell voltage-clamp experiments were performed using the Axoclamp 2A amplifier in the continuous single electrode voltage clamp mode. Pipettes (2–6 MΩ) were pulled on a Flaming/Brown P-87 (Sutter Instruments, CO) horizontal micro-electrode puller from Clark GC-150T glass (Clark Electromedical Instruments, U.K.) (seal resistance >1 GΩ). After disrupture of the patch membrane series resistance (<10 MΩ) was compensated for ~80%. With current amplitudes of <5 nA, the maximal voltage error is estimated to be <10 mV. Cell capacitance (~100 pF) was not compensated. Measurements of calcium or sodium currents were commenced 20 mins after access to the cell, in order to allow equilibration with the pipette solution. Data acquisition was controlled by a CED AD/DA converter (Cambridge Electronics Design, Cambridge, U.K.) 30 connected to an Intel 80486-based computer, run with voltage-clamp software developed in our laboratory. The current recordings were filtered at 1–5 kHz, sampled at 1 kHz (calcium currents and K+ currents) or 3 kHz (Na+ currents) and stored on-line. This system allowed simultaneous application of voltage-steps, acquisition of current recordings and timed application of toxins.

Example 2

Purification of γ-Conotoxin PnVIIA

Conus pennaceus venom was fractionated as described under Methods, and reverse-phase peptide containing fractions were assayed for γGlu content using a comparison of positive ion versus negative ion modes of MALDI mass spectrometry (Nakamura et al., 1996). The positive fraction indicated as PnVII in FIG. 1B of Fainzilber et al. (1994) was repurified by reverse phase phenyl chromatography and conotoxin-PnVIIA was obtained as the major component. On-line spectral analyses of the final chromatographic step suggested homogeneity of the purified toxin. ESI/MS measurements of the purified peptide revealed a single mass of 3718.4, further confirming homogeneity of PnVIIA.

Example 3

Chemical Characterization of γ-Conotoxin PnVIIA

Automated Edman sequencing of PnVIIA after alkylation with 4-vinylpyridine revealed a 32 amino acid sequence, allowing unambiguous assignments of 30 residues (Table 2). The extremely low yields of Glu at steps 14 and 26 further suggested the presence of γ-carboxyglutamate residues at these positions. Amino acid composition analysis (Table 3) was consistent with the proposed sequence (Table 4), and the ESI/MS measurement fits that predicted from the sequence assuming two γ-carboxyglutamate residues, three disulfide bridges and a free carboxy terminus (measured mass 3718.4, predicted 3719.0).

TABLE 2

Edman Degradation of PnVIIA

| Cycle # | Assigned Residue | Yield (pmoles) |
| --- | --- | --- |
| 1 | Asp | 185 |
| 2 | Cys | 170 |
| 3 | Thr | 180 |
| 4 | Ser | 190 |
| 5 | Trp | 170 |
| 6 | Phe | 140 |
| 7 | Gly | 210 |
| 8 | Arg | 85 |
| 9 | Cys | 93 |
| 10 | Thr | 150 |
| 11 | Val | 170 |
| 12 | Asn | 85 |
| 13 | Ser | 110 |
| 14 | Glu | 9 |
| 15 | Cys | 50 |
| 16 | Cys | 56 |
| 17 | Ser | 18 |
| 18 | Asn | 35 |
| 19 | Ser | 15 |
| 20 | Cys | 11 |
| 21 | Asp | 23 |
| 22 | Gln | 26 |
| 23 | Thr | 22 |
| 24 | Tyr | 17 |
| 25 | Cys | 14 |
| 26 | Glu | 3 |
| 27 | Leu | 17 |
| 28 | Tyr | 14 |
| 29 | Ala | 11 |
| 30 | Phe | 13 |
| 31 | Hyp | 8 |
| 32 | Ser | 9 |

TABLE 3

Amino Acid Composition Analysis of Conotoxin-PnVIIA

| Amino Acid | Mole Ratio |
| --- | --- |
| Asx | 3.9 (4) |
| Ser | 4.7 (5) |
| Glx | 3.0 (3) |
| Cys | 5.2 (6) |
| Thr | 2.8 (3) |
| Gly | 1.1 (1) |
| Arg | 1.0 (1) |
| Hyp | 0.8 (1) |
| Ala | 1.2 (1) |
| Tyr | 2.0 (2) |
| Val | 1.2 (1) |
| Phe | 2.0 (2) |
| Leu | 1.2 (1) |
| Trp | n.d (1) |

Molar ratios of amino acids determined after acid hydrolysis and FMOC derivatization. Values in brackets are those predicted from the amino acid sequence.

TABLE 4

Amino Acid Sequence of PnVIIA and TxVIIA

| | | | | | | | | | | | | | | | | | | | |
| --- | --- | --- | --- | --- | --- | --- | --- | --- | --- | --- | --- | --- | --- | --- | --- | --- | --- | --- | --- |
| PnVIIA (SEQ ID NO: 42): | D | C TSWFGR | C | T | V | N | SγCCS | | N | S | C | DQT | YC | γ | L | YAFOS—COOH |
| TxVIIA (SEQ ID NO: 43): | | C GGYSTY | C | γ | V | D | SγCCS | D | N | | C | VRS | YC | T | L | F—NH$_2$ |

Sequence identities are underlined; similarities are in bold type; and spaces inserted to maximize homologies.

In order to verify the presence of γcarboxyglutamate, and to determine the C-terminus, the peptide was further analyzed by mass spectrometry. A tryptic digest of reduced and carboxymethylated PnVIIA gave two peptides, T1 and T2, whose average molecular masses by ESI/MS were 1029.0 and 3062.6, respectively. These masses fit those predicted for the two PnVIIA tryptic peptides, namely 1029.1 for the sequence DXTSWFGR (SEQ ID NO:44), where X is carboxymethylCys, and 3062.2 for the sequence XTVNSX$_1$XXSNSXDQTYXX$_1$LYAFX$_2$S (SEQ ID NO:45), where X$_1$ is γ-carboxyglutamate and X$_2$ is 4-trans-hydroxyproline. Asp-N digest of the C-terminal tryptic peptide T2 gave two products, AN1 and AN2. ESI/MS average mass for AN1 was 1525.4, fitting the predicted mass of the Asp-N fragment XTVNSX$_1$XXSNSX (residues 1–12 of SEQ ID NO:45; predicted 1525.6). The monoisotopic LSI/MS measured mass for the C-terminal fragment AN2 was 1553.7, in agreement with the calculated value assuming the C-terminal is a free acid. An attempt to further confirm the C-terminal sequence of PnVIIA by LSI tandem MS failed, perhaps due to poor ionization efficiency of AN2. Therefore, PnVIIA was reduced and alkylated with iodoacetamide, a procedure expected to generate derivatives with better CID spectra than carboxymethylated peptides. After trypsin followed by Asp-N digests, the C-terminal carbamolmethylated peptide AN2u was isolated. Methylation with HCl/MeOH gave a tetra ester, with monoisotopic LSI/MS mass of 1608.9. This mass fits a peptide with incorporation of four methyl groups—one at the side chain of Asp, two at the carboxyl groups of the γ-carboxyglutamate, and the fourth at the presumed C-terminal free carboxyl (predicted monoisotopic mass 1608.7). The protonated tetra-methylated AN2u was further analyzed by CID mass spectrometry, giving a spectrum confining all details of the C-terminal sequence. The γ-carboxyglutamate residue is clearly indicated by the immonium ion at m/z 174, and its position revealed by the b5 and b6 molecular ions. The y2 ion confirms a C-terminal structure of —Hyp-Ser-OMe, derived from the free carboxy terminal of PnVIIA. Thus, the sequence of the peptide including the modified residues γ-carboxyglutamate and Hyp was confirmed; and the free carboxy terminus established by mass spectrometry.

PnVIIA belongs to the large group of conotoxins with the cysteine framework of ω and δ conotoxins, however, the sequence is most homologous to conotoxin-TxVIIA (Table 4). These homologies comprise approximately 48% amino acid identity and 63% similarity, including positioning of most hydrophobic and some charged residues, as well as one of the γ-carboxyglutamates.

Example 4

Biological Activity of γ-Conotoxin PnVIIA

Paralytic Activity of PnVIIA. Initial injections of PnVIIA to limpet snails (Patella) did not reveal the contractile paralysis previously observed for TxVIIA and other conotoxins in this bioassay (Fainzilber et al., 1991), however at doses above 50 pmoles/100 mg body weight some flaccidity of the foot musculature could be observed. Flaccid or relaxation paralytic effects are more easily observed in bioassays on bivalve molluscs, hence toxicity of PnVIIA was quantified in bioassays in freshwater mussels (Mytilus), as previously done for conotoxins PnIVA and PnIVB (Fainzilber et al., 1995). The ED$_{50}$ for Mytilus paralysis was 63.2 pmoles/100 mg body weight. No toxic or other effects could be observed upon injection of 1 nmole PnVEA (15-fold higher than the Mytilus ED$_{50}$) per 100 mg body weight in Gambusia fish or blowfly (Sarcophaga) larvae. Interestingly, decarboxylated PnVIIA had no observable effects on Mytilus at doses of up to five-fold the ED$_{50}$ of the native peptide.

Electrophysiological Effects of PnVIIA on Lymnaea Neuroendocrine Cells. Effects of PnVIIA were first screened in a number of mollusc or vertebrate electrophysiological preparations.

Consistent effects were observed on caudodorsal neurons from the snail *Lymnaea stagnalis*, and this system was therefore used for detailed investigations on toxin activity. The caudodorsal neurons are typical rythmic bursting cells responsible for production of egg laying hormone, and their ionic currents have been characterized exhaustively (Brussaard et al., 1991; Dreijer & Kits, 1995; Kits & Mansvelder, 1996). In the first series of experiments, PnVIIA was applied to caudodorsal neurons recorded under current clamp and the effects on membrane potential and action potential firing were investigated. It was found that PnVIIA enhances the excitability of these cells in a dose-dependent way. Thus, a dose-dependent increase in excitability of caudodorsal cells (CDCs), inducing depolarization and repetitive spiking upon application of micromolar doses of PnVIIA was seen. Cells that were silent responded to low doses (<1 $\mu$M) of the toxin by depolarization, while doses of 10 $\mu$M or more induced trains of action potentials. The number of action potentials increased with increasing doses. The duration of PnVIIA application also markedly influenced the response. In silent cells, responding with a burst of action potentials, the number of action potentials and the duration of the burst increased with increasing duration of the PnVIIA pulse. Thus, a time dependence of the excitatory effect of PnVIIA in silent CDCs, showing increased duration of spiking with increased duration of application was seen. Cells that were spontaneously active responded by a temporary increase in firing frequency, followed by an afterburst hyperpolarization during which the cell stops firing for a short period. Increasing the duration of PnVIIA application under these circumstances led to an increase in the duration of the burst, but even more so in the duration of the afterburst silent refractory period. Thus, a time dependence of the excitatory effect of PnVIIA in spontaneously active CDCs, showing that not only spiking increases but also the duration of silent period after the afterburst increases with longer applications was seen. The latter effect is possibly indirect, as a natural consequence from the increased firing frequency induced by the toxin.

Whether the effect was due to closure (blockade) or opening (activation) of ion channels was investigated by measuring input resistance of the cell membrane upon injection of hyperpolarizing current pulses (30 $\mu$A). The amplitude of the resulting hyperpolarization is a direct measure of the membrane resistance. In this experiment, pulses of hyperpolarizing current were injected into CDCs, giving rise to hyperpolarizations of the membrane potential. While the injected current is constant, the hyperpolarizing response decreases upon application of PnVIIA, showing that the membrane resistance decreases or, in other words, the membrane conductance increases. It was seen that during PnVIIA application hyperpolarization amplitude is strongly decreased (~50% attenuation), thus revealing a marked decrease in membrane resistance. Thus, PnVIIA induces an increase in conduction, i.e., leads to the opening of ion channels, and therefore acts primarily as a channel agonist or activator, rather than as a channel blocker.

In a further series of experiments, the identity of the channel(s) activated by PnVIIA was investigated. To this end, whole cell voltage clamp experiments were performed on caudodorsal neurons, however, no consistent effects of the toxin could be observed on fast voltage gated sodium or calcium currents, nor on the potassium currents that are activated in a standard voltage step protocol. A slow ramp protocol was then applied to investigate possible effects on slow voltage gated currents (also designated as pacemaker currents) that are believed to underlie spontaneous firing. In this experiment current responses to a voltage ramp protocol in standard HBS during which the membrane potentials go from −80 to +20 mV at a rate of mV/s (control) were measured. This protocol will only reveal slow, voltage-gated currents, as fast currents will inactivate during the slow voltage ramp. An inward current is activated at ∼−30 mV and more positive. Most likely, this represents a pacemaker current. With 10 μM PnVIIA (10 μM) the voltage dependence shifts to the left (i.e., the current activates already at more hyperpolarized potentials). Furthermore, an increase in outward current at >∼0 mV occurs. Thus, the experiments indicated that a noninactivating inward current is activated at voltages above 30 mV to the voltage ramp protocol. Preliminary experiments indicate that this inward current is a nonspecific cation current that is reduced in $Na^+$ free selective saline and completely blocked by 1 mM $Ni^{2+}$. Thus, most likely, $Na^+$ and $Ca^{2+}$ carry the inward current. In voltage dependence and ion selectivity, this current strongly resembles a pacemaker current in other Lymnaea neurons elaborately described by van Soest and Kits (1997). In the presence of 10 μM PnVIIA, a dual effect was observed. First, the activation range of the slow inward current shifted by ∼10 mV to a more negative potential, thus accounting for the enhanced excitability of the cells. Second, we saw an increase in noninactivating outward current at potentials above 0 mV. Whether the latter is a direct effect of PnVIIA, or an indirect effect due to the increased inward current, remains to be determined. It is, however, in line with the previously observed prolongation of afterburst hyperpolarization under current clamp conditions. These data show that the primary event mediating the excitatory effects of PnVIIA on Lymnaea caudodorsal neurons is an enhancement of a slow, voltage-activated inward cation channel.

Example 5

Isolation of a γ-Conotoxin Tx6.4 from *Conus textile*

A *Conus textile* cDNA library was prepared from venom duct using conventional techniques. DNA from single clones was amplified by conventional techniques using primers which correspond approximately to the M13 universal priming site and the M13 reverse universal priming site. The primers which were used are:

5'-TTTCCCAGTCACGACGTT-3' (SEQ ID NO:46) and
5'-CACACAGGAAACAGCTATG-3' (SEQ ID NO:47).

Clones having a size of approximately 300 nucleotides were sequenced and screened for similarity in sequence to PnVIIA and TxVIIA. A DNA was isolated having the sequence set forth in SEQ ID NO: 16, which encoded the propeptide sequence set forth in SEQ ID NO: 17. This new γ-conotoxin has the sequence described above and set forth in SEQ ID NO:7. Preferably, $Xaa_1$ is Trp, $Xaa_2$ is γ-Glu and $Xaa_3$ is Hyp. The C-terminus preferably contains a free hydroxyl group.

Example 6

Isolation of γ-Conopeptides

The procedure of Example 5 was followed to isolate additional nucleic acids encoding γ-conopeptides. The nucleic acids which were isolated have the nucleotide sequences set forth in SEQ ID NOs: 18, 20, 22, 24, 26, 28, 30, 32 and 34. These nucleic acids encode the propeptides having the amino acid sequences set forth in SEQ ID NOs:19, 21, 23, 25, 27, 29, 31, 33 and 35, respectively. The mature peptide sequences are set forth in SEQ ID NOs:8–15 and 36.

Example 7

Biological Activity of γ-Conotoxin TxVIIA

Isolated medial neurons from *Aplysia oculifera* pleuropedal ganglia (Kehoe, 1972) were cultured as previously described (Schacher & Proshansky, 1983). The neurons were cultured at very low densities to prevent any possible synaptic interactions among them. Passive and active membrane properties of the cultured neurons were studied using conventional intracellular recording and stimulation techniques. Briefly, the cell body of a cultured neuron was impaled by two microelectrodes filled with 2 M KCl (5–10 MΩ resistance), one for current injection and the other for voltage recording. Analysis of the resting potential, input resistance, and action potential amplitude and shape was carried out in artificial sea water composed of 460 nM NaCl, 10 mM KCl, 11 mM $CaCl_2$, 55 mM $MgCl_2$ and 10 mM Hepes, pH 7.6. Venom fractions for electrophysiological experiments were dissolved in artificial sea water containing 10 mg/ml bovine serum albumin. The Sephadex™ G-50 fraction was applied at 100–200 μg/ml and purified toxin at final concentrations of 0.25–0.5 μM.

The effects of venom fractions and purified toxin on isolated Aplysia neurons were characterized by measuring the resting potential, input resistance and action potential amplitude and shape. The Vt fraction from the Sephadex™ G-50 column (G-50-Vt) (Fainzilber et al., 1991) and the purified toxin revealed significant effects at concentrations of 100 μg/ml and 0.25–0.5 μM, respectively. The effects of G-50-Vt, TxIA and TxIB were essentially similar Fainzilber et al., 1991). These fractions induced a transient membrane depolarization of 5–12 mV for 40–120 s. Within 3–30 s. after bath application of the toxin, the quiescent neurons fired spontaneously. Concomitantly, the action potential duration increased by one to two orders of magnitude, extending in many experiments to over 1 s. The prolonged action potentials are typically composed of an initial spike with a prolonged shoulder. In the continuous presence of the toxin in the bathing solution, the action potential duration gradually recovers. 20–30 min. after toxin application, the action potential duration was only 50–100% longer than in the control. Throughout this period, the threshold for action potential initiation was reduced. The changes in membrane excitability and action potential duration induced by the toxins were completely reversible upon washing of the neuron with artificial sea water. TxI-induced prolongation of the action potential duration was observed also when $Ca^{2+}$ and $K^+$ conductances were blocked ($Ca^{2+}$ free artificial sea water, 16 mM $Ca^{2+}$ and 50 mM tetraethylammonium, 150 μM 3,4-diaminopyridine and 10 nM Cs). Addition of tetrodotoxin (10 μM) under these conditions reduced the TxI-induced spike prolongation. TxVIIA induced similar effects on the membrane properties of isolated neurons, including membrane depolarization and repetitive firing. However, TxVIIA did not cause any increase in action potential duration.

The amino acid sequence of PnVIIA conserves the six-cysteine, four-loop framework C . . . C . . . CC . . . C . . . C typical of ω and δ conotoxins, and as shown in Table 4, is most homologous to the sequence of conotoxin-TxVIIA, an excitatory toxin from *Conus textile* venom (Fainziber et al., 1991; Nakarnura et al., 1996). Both of these toxins have an identical, extremely acidic net charge (−5) and are similar in their surface hydrophobic/hydrophilic interaction properties, as evidenced by comparable elusion properties in reverse-phase chromatography. Furthermore, the grow effects of these toxins in their respective sensitive systems (Aplysia versus Lymnaea neurons) are very similar, comprising an enhancement of excitability decreased membrane resistance, and increased repetitive firing. PnVIIA and TxVIIA may therefore represent closely related members of the same family, or convergent evolution to closely related receptor/channel targets.

The paralytic activities of both TxVIIA and PnVIIA in their respective bioassays are markedly decreased upon decarboxylation of the γGlu residues. Although the primarily structural importance of γGlu-metal chelates in mammalian vitamin K-dependent blood coagulation proteins and in mollusc conantokins is well established (Freedman et al., 1995; Skjaerbaek et al., 1997), there is also evidence, for example, in prothrombin of a functional role of individual γGlu residues in membrane binding (Ratcliffe et al., 1993). Although the 3-D structures of conotokins TxVIIA and γPnVIIA are most likely directed and stabilized by the three disulfide bonds, as in conotoxins in general, we cannot rule out at this stage a secondary microstructural role of the γGlu residues. However, an attractive hypothesis is that the γGlu residues in these peptides form part of a membrane or receptor recognition patch, with other variable residues (Table 4) providing specific recognition for channel isoforms or subtypes. Hypervariability in structurally related conotoxins is a well established mediator of the exquisite selectivity of these peptides for receptor subtypes (Myers et al., 1993; Nielsen et al., 1996).

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Betner, I., & Foldi, P. (1986). *Chromatographia* 22:381–387.

Bodansky et al. (1966). *Chem. Ind.* 38:1597–98.

Brussaard, A. B. et al. (1991). *J. Physiol.* 441:385–404.

Burlingame, A. L. (1994). In *Biological Mass Spectrometry, Present and Future* (Matquo, T., et al., Eds.) pp. 147–164, Wiley, Chichester.

Cartier, G. E. et al. (1996). *J. Biol. Chem.* 271:7522–7528.

Cruz, L. J. at al. (1976). *Verliger* 18:302–308.

Cruz, L. J. et al. (1987). *Conus geographus* toxins that discriminate between neuronal and muscle sodium channels. *J. Biol. Chem.* 260:9280–9288.

Dreijer, A. M., & Kits, K. S. (1995). *Neuroscience* 64:787–800.

Fainzilber, M. et al. (1991). *Eur. J. Biochem.* 202:589–596.

Fainzilber M. et al. (1994). *J. Biol. Chem.* 269:2574–2580.

Fainzilber, M. et al. (1994). *Biochemistry* 33:9523–9529.

Fainzilber M. et al. (1995). *J. Biol. Chem.* 270:1123–1129.

Fainzilber M. et al. (1995). *Biochemistry* 34:8649–8656.

Freedman, S. J., Furie, B. C., Furie B. & Baleja J. D. (1995). *Biochemistry* 35:12126–12137.

Haack, J. A. et al. (1990). Contryphan-T: a gamma-carboxyglutamate containing peptide with N-methyl-d-aspartate antagonist activity. *J. Biol. Chem.* 265:6025–6029.

Hoehn, K., Watson, T. W. J. & MacVicar, B. A. (1993) *Neuron* 10:543–552.

Horiki, K. et al. (1978). *Chemistry Letters* 165–68.

Kaiser et al. (1970). *Anal. Biochem.* 34:595.

Kapoor(1970). *J. Pharm. Sci.* 59:1–27.

Kits K. S., & Mansvelder H. D. (1996). *Invertebrate Neuroscience* 2:9–34.

Kornreich, W. D. et al. (1986). U.S. Pat. No. 4,569,967.

Medzihradszky, K. F. et al. (1994). *J. Am. Soc. Mass Spectrom.* 5:350–358.

Mena, E. E. et al. (1990). Contryphan-G: a novel peptide antagonist to the N-methyl-D-aspartic acid (NMDA) receptor. *Neurosci. Lett.* 118:241–244.

*Methoden der Organischen Chemie* (Houben-Weyl): *Synthese von Peptiden*, E. Wunsch (Ed.), Georg Thieme Verlag, Stuttgart, Ger. (1974).

Myers, R. A., Ctuz, L. J., Rivier, J. & Olivera, B. M. (1993). *Chem. Rev.* 93, 1923–36.

Nakamura, T. et al. (1996). *Protein Science* 5:524–530.

Nielsen, K. J., Thomas, L., Lewis, R. J., Alewood, P. F., Craik, D. J. (1996). *J. Mol. Biol.* 263:297–310.

Nishiuchi, Y. et al. (1993). Synthesis of gamma-carboxyglutamic acid-containing peptides by the Boc strategy. *Int. J. Pept. Protein Res.* 42:533–538.

Olivera, B. M. et al. (1984). U.S. Pat. No. 4,447,356.

Olivera, B. M. et al. (1985). Peptide neurotoxins from fish-hunting cone snails. *Science* 230:1338–1343.

Olivera, B. M. et al. (1996). U.S. Pat. No. 5,514,774.

Olivera, B. M. et al. (1997). U.S. Pat. No. 5,591,821.

Partridge, L. D. & Swandulla, D. (1988). *Trends Neurosci.* 11:69–72.

Ratcliffe, J. V., Furie, B., Furie, B. C. (1993). *J. Biol. Chem.* 268:24339–24345.

*Remington's Pharmaceutical Science*, 17th Ed., Mack Publishing Co., Easton, Pa. (1985).

Rivier, J. R. et al. (1978). *Biopolymers* 17:1927–38.

Rivier, J. R. et al. (1987). Total synthesis and further characterization of the gamma-carboxy-glutamate-containing 'sleeper' peptide from *Conus geographus. Biochem.* 26:8508–8512.

Roberts et al. (1983). *The Peptides* 5:342–429.

Reuter, H. (1984). *Annual Rev. Physiol.* 46:473–484.

Sambrook, J. et al. (1979). *Molecular Cloning. A Laboratory Manual*, 2nd Ed., Cold Spring Harbor Laboratory, Cold Spring Harbor, N.Y.

Schroder & Lubke (1965). *The Peptides* 1:72–75, Academic Press, NY.

Skjaerbaek, N., Nielsen, K. J., Lewis, R. J., Alewood, P., Craik, D. J. (1997). *J. Biol Chem.* 272:291–2299.

Stewart and Young, *Solid-Phase Peptide Synthesis*, Freeman & Co., San Francisco, Calif. (1969).

Vale et al. (1978). U.S. Pat. No. 4,105,603.

van Soest, P. F. & Kits, K. S. (1997). *J. Neurophysiol.*

Wilson, G. F. & Kaczmarek, L. K. (1993). *Nature* 366:433–448.

Zhou L. M., et al. (1996a). Synthetic Analogues of Contryphan-G: NMDA Antagonists Acting Through a Novel Polyamine-Coupled Site. *J. Neurochem.* 66:620–628.

U.S. Pat. No. 3,972,859 (1976).

U.S. Pat. No. 3,842,067 (1974).

U.S. Pat. No. 3,862,925 (1975).

PCT Published Application WO 96/11698

What is claimed is:

1. A substantially pure conopeptide selected from the group consistng of:

(a) PnVIIA: Asp-Cys-Thr-Ser-Xaa$_1$-Phe-Gly-Arg-Cys-Thr-Val-Asn-Ser-Xaa$_2$-Cys-Cys-Ser-Asn-Ser-Cys-Asp-Gln-Thr-Tyr-Cys-Xaa$_2$-Leu-Tyr-Ala-Phe-Xaa$_3$-Ser (SEQ ID NO:6) wherein Xaa$_1$ is Trp, Xaa$_2$ is γ-Glu, Xaa$_3$ is Hyp and the C-terminus has a free carboxyl group;

(b) Tx6.4: Xaa$_1$-Leu-Xaa$_2$-Cys-Ser-Val-Xaa$_1$-Phe-Ser-His-Cys-Thr-Lys-Asp-Ser-Xaa$_2$-Cys-Cys-Ser-Asn-Ser-Cys-Asp Gln-Thr-Tyr-Cys-Thr-Leu-Met-Xaa$_3$-Xaa$_3$-Asp-Xaa$_1$ (SEQ ID NO:7) wherein Xaa$_1$ is Trp, Xaa$_2$ is γ-Glu, Xaa$_3$ is Hyp and the C-terminus has a free carboxyl group;

(c) Tx6.9: Xaa$_1$-Xaa$_1$-Arg-Xaa$_1$-Gly-Gly-Cys-Met-Ala-Xaa$_1$-Phe-Gly-Leu-Cys-Ser-Arg-Asp-Ser-Xaa$_2$-Cys-Cys-Ser-Asn-Ser-Cys-Asp-Val-Thr-Arg-Cys-Xaa$_2$-Leu-Met-Xaa$_3$-Phe-Xaa$_3$-Xaa$_3$-Asp-Xaa$_1$ (SEQ ID NO:8) wherein Xaa$_1$ is Trp, Xaa$_2$ is γ-Glu, Xaa$_3$ is Hyp and the C-terminus has a free carboxyl group;

(d) Tx6.6: Asp-Xaa$_1$-Xaa$_1$-Asp-Asp-Gly-Cys-Ser-Val-Xaa$_1$-Gly-Xaa$_3$-Cys-Thr-Val-Asn-Ala-Xaa$_2$-Cys-Cys-Ser-Gly-Asp-Cys-His-Xaa$_1$-Thr-Cys-Ile-Phe-Gly-Xaa$_1$-Xaa$_2$-Val (SEQ ID NO:10) wherein is Xaa$_1$ is Trp, Xaa$_2$ is γGlu, Xaa$_3$ is Hyp and the C-terminus has a free carboxyl group;

(e) Gm6.7: Xaa$_2$-Cys-Arg-Ala-Xaa$_1$-Tyr-Ala-Xaa$_3$-Cys-Ser-Xaa$_3$-Gly-Ala-Gln-Cys-Cys-Ser-Leu-Leu-Met-Cys-Ser-Lys-Ala-Thr-Ser-Arg-Cys-Ile-Leu-Ala-Leu (SEQ ID NO:12) wherein Xaa$_1$ is Trp, Xaa$_2$ is γ-Glu, Xaa$_3$ is Hyp and the C-terminus has a free carboxyl group;

(f) Mr6.1: Asn-Gly-Gln-Cys-Xaa$_2$-Asp-Val-Xaa$_1$-Met-Xaa$_3$-Cys-Thr-Ser-Asn-Xaa$_1$-Xaa$_2$-Cys-Cys-Ser-Leu-Asp-Cys-Xaa$_2$-Met-Tyr-Cys-Thr-Gln-Ile (SEQ ID:13) wherein Xaa$_1$ is Trp, Xaa$_2$ is γ-Glu, Xaa$_3$ is Hyp and the C-terminus is amidated;

(g) Mr6.2: Cys-Gly-Gly-Xaa$_1$-Ser-Thr-Tyr-Cys-Xaa$_2$-Val-Asp-Xaa$_2$-Xaa$_2$-Cys-Cys-Ser-Xaa$_2$-Ser-Cys-Val-Arg-Ser-Tyr-Cys-Thr-Leu-Phe (SEQ ID NO:14) wherein Xaa$_1$ is Trp, Xaa$_2$ is γ-Glu and the C-terminus is amidated; and (h) Mr6.3: Asn-Gly-Gly-Cys-Lys-Ala-Thr-Xaa$_1$-Met-Ser-Cys-Ser-Ser-Gly-Xaa$_1$-Xaa$_2$-Cys-Cys-Ser-Met-Ser-Cys-Asp-Met-Try-Cys (SEQ ID NO:15) wherein Xaa$_1$ is Trp, Xaa$_2$ is γ-Glu and the C-terminus is amidated.

2. The conopeptide of claim 1, wherein the conopeptide is PnVIIA (SEQ ID NO:6) and wherein Xaa$_1$ is Trp, Xaa$_2$ is γ-Glu, Xaa$_3$ is Hyp and the C-terminus has a free carboxyl group.

3. The conopeptide of claim 1, wherein the conopeptide is Tx6.4 (SEQ ID NO:7) and wherein Xaa$_1$ is Trp, Xaa$_2$ is γ-Glu, Xaa$_3$ is Hyp and the C-terminus has a free carboxyl group.

4. The conopeptide of claim 1, wherein the conopeptide is Tx6.9 (SEQ ID NO:8) and wherein Xaa$_1$ is Trp, Xaa$_2$ is γ-Glu, Xaa$_3$ is Hyp and the C-terminus has a free carboxyl group.

5. The conopeptide of claim 1, wherein the conopeptide is Tx6.6 (SEQ ID NO: 10) and wherein Xaa$_1$ is Trp, Xaa$_2$ is γ-Glu, Xaa$_3$ is Hyp and the C-terminus has a free carboxyl group.

6. The conopeptide of claim 1, wherein the conopeptide is Gm6.7 (SEQ ID NO:12) and wherein Xaa$_1$ is Trp, Xaa$_2$ is γ-Glu, Xaa$_3$ is Hyp and the C-terminus has a free carboxyl group.

7. The conopeptide of claim 1, wherein the conopeptide is Mr6.1 (SEQ ID NO:13) and wherein Xaa$_1$ is Trp, Xaa$_2$ is γ-Glu, Xaa$_3$ is Hyp and the C-terminus is amidated.

8. The conopeptide of claim 1, wherein the conopeptide is Mr6.2 (SEQ ID NO:14) and wherein Xaa$_1$ is Trp, Xaa$_2$ is γ-Glu and the C-terminus is amidated.

9. The conopeptide of claim 1, wherein the conopeptide is Mr6.3 (SEQ ID NO: 15) and wherein Xaa$_1$ is Trp, Xaa$_1$ is γ-Glu and the C-terminus is amidated.

* * * * *